(12) United States Patent
Ouchi

(10) Patent No.: US 10,558,030 B2
(45) Date of Patent: Feb. 11, 2020

(54) STRUCTURES ILLUMINATION MICROSCOPY SYSTEM, METHOD, AND NON-TRANSITORY STORAGE MEDIUM STORING PROGRAM

(71) Applicant: NIKON CORPORATION, Tokyo (JP)

(72) Inventor: Yumiko Ouchi, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 13 days.

(21) Appl. No.: 15/832,203

(22) Filed: Dec. 5, 2017

(65) Prior Publication Data
US 2018/0164571 A1    Jun. 14, 2018

Related U.S. Application Data

(63) Continuation of application No. PCT/JP2015/002870, filed on Jun. 8, 2015.

(51) Int. Cl.
*H04N 7/18* (2006.01)
*G02B 21/36* (2006.01)
(Continued)

(52) U.S. Cl.
CPC .......... *G02B 21/367* (2013.01); *G01N 21/64* (2013.01); *G01N 21/6458* (2013.01); *G02B 21/0032* (2013.01); *G02B 21/0056* (2013.01); *G02B 21/0076* (2013.01); *G02B 21/0088* (2013.01); *G02B 21/082* (2013.01); *G02B 21/16* (2013.01); *G02B 21/361* (2013.01); *G02B 27/58* (2013.01)

(58) Field of Classification Search
CPC ........................................................ G02B 21/06
USPC ...................................................... 348/79–80
See application file for complete search history.

(56) References Cited

U.S. PATENT DOCUMENTS

| | | | |
|---|---|---|---|
| 6,239,909 B1 | 5/2001 | Hayashi et al. |
| 6,376,818 B1 | 4/2002 | Wilson et al. |
| 8,081,378 B2 | 12/2011 | Osawa et al. |
| 8,115,806 B2 | 2/2012 | Osawa et al. |

(Continued)

FOREIGN PATENT DOCUMENTS

| | | |
|---|---|---|
| JP | 2007-108154 A | 4/2007 |
| JP | 2012-504252 A | 2/2012 |

(Continued)

OTHER PUBLICATIONS

Sep. 25, 2018 Office Action issued in Japanese Patent Application No. 2017-522754.

(Continued)

*Primary Examiner* — Anand S Rao
(74) *Attorney, Agent, or Firm* — Oliff PLC

(57) ABSTRACT

A structured illumination microscopy system including an illumination optical system illuminating excitation light to excite a fluorescent material contained in a sample on the sample with an interference fringe; a controlling part controlling a direction, a phase, and a spatial frequency of the interference fringe; an image-forming optical system forming an image of the sample which is modulated by illumination of the interference fringe; an imaging sensor capturing the image formed by the image-forming optical system; and a demodulating part performing demodulation processing by using a plurality of images captured by the imaging sensor in which the controlling part controls the spatial frequency of the interference fringe in accordance with an illuminating position of the interference fringe.

14 Claims, 17 Drawing Sheets

(51) Int. Cl.
*G01N 21/64* (2006.01)
*G02B 21/00* (2006.01)
*G02B 21/08* (2006.01)
*G02B 21/16* (2006.01)
*G02B 27/58* (2006.01)

(56) References Cited

U.S. PATENT DOCUMENTS

| | | |
|---|---|---|
| 2009/0086314 A1 | 4/2009 | Namba et al. |
| 2011/0182529 A1 | 7/2011 | Kempe et al. |
| 2014/0055594 A1* | 2/2014 | Nomura ............ G02B 21/06 348/79 |

FOREIGN PATENT DOCUMENTS

| | | |
|---|---|---|
| JP | 2015-505039 A | 2/2015 |
| WO | 2007/139201 A1 | 12/2007 |
| WO | 2013/105922 A2 | 7/2013 |
| WO | 2015/052920 A1 | 4/2015 |

OTHER PUBLICATIONS

Wicker, K. et al., "Phase optimisation for structured illumination microscopy," Optics Express, vol. 21, No. 2, Jan. 28, 2013.

Kner, P. et al., "Super-resolution video microscopy of live cells by structured illumication," Nature Methods, vol. 6, No. 5, May 2009, pp. 339-344.

Sep. 8, 2015 International Search Report issued in International Patent Application No. PCT/JP2015/002870.

Dec. 12, 2017 International Preliminary Report on Patentability issued in International Patent Application No. PCT/JP2015/002870.

Jul. 2, 2019 Office Action issued in Japanese Patent Application No. 2017-522754.

* cited by examiner in case of the cell (water)

| depth[μ m] | 0-0.5 | 0.5-1 | 1-2 | 2-5 | 5-10 |
|---|---|---|---|---|---|
| fringe spatial frequency [c/mm] | 40 | 35 | 30 | 25 | 20 |
| super-resolution effect ε | 1.8 | 1.7 | 1.6 | 1.5 | 1.4 |

FIG.9 in case of a mounting medium

| depth[μ m] | 0-1.8 | 1.8-3.6 | 3.6-7.2 | 7.2-18 | 18-36 |
|---|---|---|---|---|---|
| fringe spatial frequency [c/mm] | 40 | 35 | 30 | 25 | 20 |
| super-resolution effect ε | 1.8 | 1.7 | 1.6 | 1.5 | 1.4 |

FIG.10

STRUCTURES ILLUMINATION MICROSCOPY SYSTEM, METHOD, AND NON-TRANSITORY STORAGE MEDIUM STORING PROGRAM

CROSS-REFERENCE TO RELATED APPLICATION

This application is a continuation application of International Application No. PCT/JP2015/002870, filed Jun. 8, 2015, designating the U.S., the entire contents of which are incorporated herein by reference.

BACKGROUND

1. Field

The present application relates to a structured illumination microscopy system, a method, and a non-transitory storage medium storing program.

2. Description of the Related Art

A super-resolution microscopy is effective for observation of a specimen such as living cells. A structured illumination microscopy (SIM) being one kind of the super-resolution microscopies is a technology modulating information of a microstructure having high spatial frequency into a frequency capable of being transmitted to an image side of an objective lens by illuminating the specimen with an interference fringe (for instance, refer to Specification of U.S. Pat. No. 6,239,909). However, it turned out that an image quality of a super-resolved image at a specimen deep part generated by the SIM tends to be worse compared to a super-resolved image at a specimen surface.

SUMMARY

A structured illumination microscopy system of one embodiment of the present application includes an illumination optical system illuminating excitation light to excite a fluorescent material contained in a sample on the sample with an interference fringe; a controlling part controlling a direction, a phase, and a spatial frequency of the interference fringe; an image-forming optical system forming an image of the sample which is modulated by illumination of the interference fringe; an imaging sensor capturing the image formed by the image-forming optical system; and a demodulating part performing demodulation processing by using a plurality of images captured by the imaging sensor, in which the controlling part controls the spatial frequency of the interference fringe in accordance with an illuminating position of the interference fringe.

A method of one embodiment of the present application includes illuminating excitation light to excite a fluorescent material contained in a sample on the sample with an interference fringe; controlling a direction, a phase, and a spatial frequency of the interference fringe; capturing images of the sample modulated by illumination of the interference fringe; performing demodulation processing by using a plurality of images being captured; and controlling the spatial frequency of the interference fringe in accordance with an illuminating position of the interference fringe.

A non-transitory storage medium storing a program of one embodiment of the present application causes a computer to execute processing controlling a spatial frequency of an interference fringe in accordance with an illuminating position of the interference fringe, in a structured illumination microscopy system captures an image of a sample modulated by illumination of the interference fringe and performs demodulation processing.

BRIEF DESCRIPTION OF THE DRAWINGS

FIG. 6A is a diagram illustrating a pattern example of a three-beam mask when allowing 0th-order diffractive light flux and the ±first-order diffractive light fluxes to pass through.

FIG. 6B is a diagram illustrating a pattern example of a two-beam mask 18 when allowing the ±first-order diffractive light fluxes to pass through.

FIG. 9 is a diagram illustrating a relationship between a depth of an observational object plane P and a proper value of a spatial frequency of interference fringe (when water is used).

FIG. 10 is a diagram illustrating a relationship between a depth of an observational object plane P and a proper value of a spatial frequency of interference fringe (when a mounting medium is used).

DETAILED DESCRIPTION OF THE EMBODIMENT

First Embodiment

Hereinafter, a structured illumination microscopy using a two-beam interference (2D-SIM: two-dimensional structured illumination microscopy) system will be described as a first embodiment of the present invention. Note that in the following description, the structured illumination microscopy system may be simply called the 2D-SIM.

Figure 1:
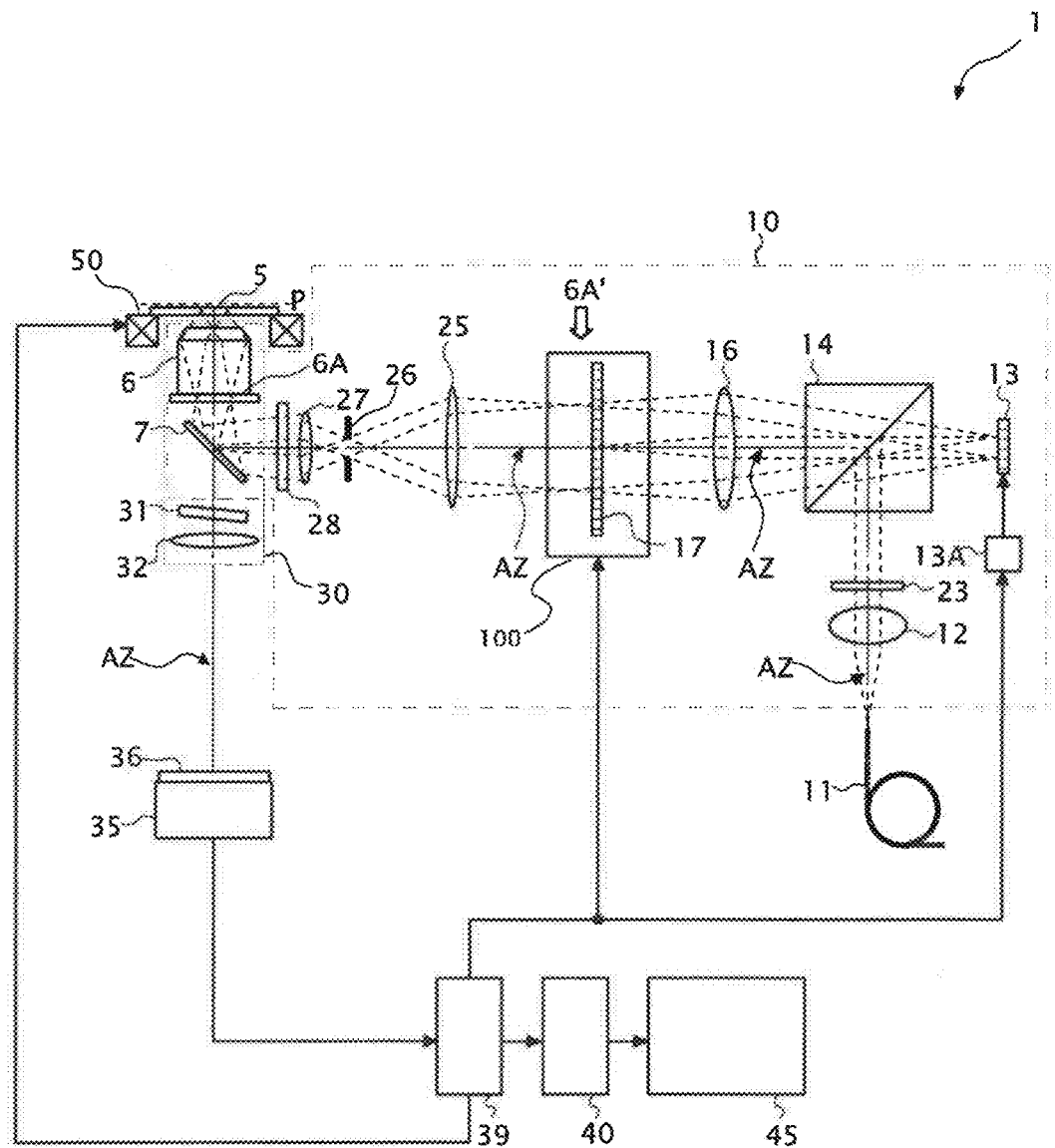
FIG. 1 is a configuration diagram of a 2D-SIM in a first embodiment.

FIG. 1 is a configuration diagram of a 2D-SIM1 (a structured illumination microscopy system 1). As illustrated in FIG. 1, there are disposed an optical fiber 11, an illumination optical system 10, an image-forming optical system 30, an imaging sensor 35, a controlling device 39, an image storing-calculating device 40, an image displaying device 45, a stage 50, and a specimen 5 in the 2D-SIM1.

The optical fiber 11 is, for example, a polarization plane maintaining type single-mode fiber to relay laser light between a not-illustrated coherent light source and the illumination optical system 10. As the coherent light source, there can be used a laser unit or the like capable of emitting a plurality kinds of laser light with different wavelengths, but the wavelength of the laser light emitted from the coherent light source is assumed to be only one kind for the sake of simplicity.

The illumination optical system 10 is, for example, an epi-illumination optical system illuminating the specimen 5 placed on the stage 50 with laser light. There are disposed a collector lens 12, a polarizing plate 23, a polarization beam splitter (PBS) 14, a diffraction grating 13, a collecting lens 16, a beam selecting part 100, a collecting lens 25, a field stop 26, a field lens 27, an excitation filter 28, a dichroic mirror 7, and an objective lens 6 in the illumination optical system 10.

The diffraction grating 13 of the illumination optical system 10 is, for example, a reflective liquid crystal SLM. Here, the diffraction grating 13 is assumed to be the reflective liquid crystal SLM, and it is called an "SLM 13". A driver 13A being a liquid crystal drive circuit is connected to the SLM 13.

The image-forming optical system 30 is an image-forming optical system forming an image of the specimen 5 on an imaging plane 36 of the imaging sensor 35. There are disposed the objective lens 6, the dichroic mirror 7, a barrier filter 31, and a secondary objective lens 32 in the image-forming optical system 30. The objective lens 6 and the dichroic mirror 7 of the image-forming optical system 30 are also used in the illumination optical system 10.

The objective lens 6 is, for example, a liquid-immersion objective lens such as an oil-immersion type, and the specimen 5 is a living cell such as a cultured cell and a tissue section with a thickness of, for example, several m to several dozen μm.

Figure 7A:
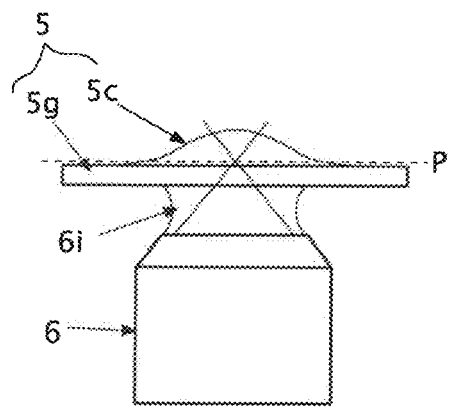
FIG. 7A is a diagram explaining a relationship between an objective lens and a specimen during a surface observation time.

Here, as illustrated in later-described FIG. 7A, the specimen 5 is assumed to be made of a parallel-plate cover glass 5g and a culture fluid 5c dropped on a surface of the cover glass 5g. A living cell is cultured in the culture fluid 5c, and fluorescent materials exhibit in the living cell. The wavelength of the coherent light source is set to the same value as an excitation wavelength of the fluorescent materials. Note that a sign 61 in FIG. 7A represents an immersion liquid (oil).

Returning to FIG. 1, the imaging sensor 35 is a two-dimensional imaging sensor such as a CCD and a CMOS, and generates an image (a later-described modulated image) by capturing an image formed on the imaging plane 36. The image generated by the imaging sensor 35 is taken into the image storing-calculating device 40 through the controlling device 39.

The stage 50 supports the specimen 5, and adjusts a space between the objective lens 6 and the specimen 5 by moving the specimen 5 along an optical axis AZ of the objective lens 6. A depth of a focal plane P of the objective lens 6 at the specimen 5 is thereby adjusted (refer to FIG. 7A and FIG. 7B). The focal plane P is an observational object plane of the 2D-SIM1. Hereinafter, the focal plane P of the objective lens 6 is called an "observational object plane P".

The controlling device 39 controls the driver 13A and the beam selecting part 100, the imaging sensor 35, the stage 50 and the not-illustrated coherent light source, and acquires a plurality pieces of modulated images necessary for super-resolution.

The image storing-calculating device 40 generates a super-resolved image based on the plurality pieces of modulated images acquired by the controlling device 39, and displays on a not-illustrated display device.

Next, behavior of light in the 2D-SIM1 is described.

Laser light exited from the not-illustrated coherent light source propagates in the optical fiber 11, then forms a point light source at an exit end of the optical fiber 11, and exits from the point light source as a divergent light flux. The divergent light flux is converted into a collimated light flux by the collector lens 12, and then adjusts a polarizing direction by passing through the polarizing plate 23. The collimated light flux whose polarizing direction is adjusted is incident on the PBS 14, reflected on a polarization separation plane of the PBS 14, and then incident on the SLM 13 from a front side.

An axis of the polarizing plate 23 is set such that the collimated light flux directed from the polarizing plate 23 to the polarization separation plane of the PBS 14 becomes S-polarization. The collimated light flux directed to the polarization separation plane of the PBS 14 is thereby guided to the SLM 13 with high efficiency.

The collimated light flux incident on the SLM 13 is diffraction-reflected by the SLM 13, and is branched into a plurality of diffractive light fluxes having different angles. In FIG. 1, only three light fluxes of a 0th-order diffractive light flux, a first-order diffractive light flux, and a −first-order diffractive light flux are illustrated out of the plurality of diffractive light fluxes.

The plurality of diffractive light fluxes exited from the SLM 13 are incident on the PBS 14, penetrate through the polarization separation plane of the PBS 14, and then are incident on the collecting lens 16 from mutually different angles.

The plurality of diffractive light fluxes incident on the collecting lens 16 are subjected to a collecting action of the collecting lens 16, and collected toward a pupil conjugate plane 6A' at mutually different positions.

Note that the pupil conjugate plane 6A' is a plane conjugate with a pupil plane 6A of the objective lens 6 with respect to the field lens 27 and the collecting lens 25. A plane which is determined by a person skilled in the art by taking design requirements such as an aberration, vignetting and the like of the objective lens 6, the field lens 27, the collecting lens 25, and so on into consideration, also falls into the concept of "the conjugate plane".

Here, the plurality of diffractive light fluxes directed to the pupil conjugate plane 6A' through the collecting lens 16 are incident on the beam selecting part 100. The beam selecting part 100 of the 2D-SIM 1 allows ±first-order diffractive light fluxes to pass through out of the received diffractive light fluxes, and shields the 0th-order diffractive light flux and high-order diffractive light fluxes of a second-order or higher. A configuration example of the beam selecting part 100 will be described in FIG. 4.

The ±first-order diffractive light fluxes passing through the beam selecting part 100 are subjected to a collecting action of the lens 25, then incident on an image conjugate plane from mutually different angles, and form a first image of the SLM 13 on the image conjugate plane.

The image conjugate plane is a plane conjugate with a focal plane (=observational object plane P) of the objective lens 6 with respect to the objective lens 6 and the field lens 27. Incidentally, the field stop 26 is disposed at the image conjugate plane.

The respective ±first-order diffractive light fluxes exited from the image conjugate plane are converted into converging light fluxes by the field lens 27, reflected by the dichroic mirror 7 after passing through the excitation filter 28, and collected toward mutually different positions of the pupil plane 6A of the objective lens 6.

The respective ±first-order diffractive light fluxes exited from the pupil plane 6A as divergent light fluxes exit from a tip of the objective lens 6 as collimated light fluxes, are incident on the focal plane (=observational object plane P) of the objective lens 6 with a predetermined angle relationship to form striped interference fringe.

The interference fringe correspond to a second image of the SLM 13 formed by the collecting lens 16, the collecting lens 25, the field lens 27 and the objective lens 6. That is, all of the collecting lens 16, the collecting lens 25, the field lens 27, and the objective lens 6 have a function of a "projecting optical system" which project the image of the SLM 13 on the observational object plane P.

The interference fringe projected on the observational object plane P have a function of shifting a spatial frequency held by a density distribution of fluorescent materials at the observational object plane P toward a lower frequency to an extent of a size of a spatial frequency K of the interference fringe, and transmitting minute structural information of the fluorescent materials to an image side of the objective lens 6.

Fluorescence generated at each position of the observational object plane P is incident on the tip of the objective lens 6, exits as a collimated light flux, and is incident on the secondary objective lens 32 through the dichroic mirror 7 and the barrier filter 31.

The collimated light flux incident on the secondary objective lens 32 is subjected to a collecting action of the secondary objective lens 32, and forms a fluorescence image of the observational object plane P on the imaging plane 36 of the imaging sensor 35.

This fluorescence image is a modulated image which is modulated by an interference fringe pattern.

The fluorescence image on the imaging plane 36 is imaged by the imaging sensor 35. Note that the image acquired by this imaging is a "modulated image" where the interference fringe patterns are superimposed. This modulated image is taken into the image storing-calculating device 40 through the controlling device 39, and a demodulating calculation is performed at the image storing-calculating device 40 (for example, the demodulating calculation described in Specification of U.S. Pat. No. 8,115,806). A fluorescence super-resolved image of the observational object plane P is generated as a result of the demodulating calculation. This fluorescence super-resolved image is stored in an internal memory (not-illustrated) of the image storing-calculating device 40 and displayed on the image display device 45.

In the 2D-SIM1, the excitation filter 28 has a function of transmitting light with the same wavelength as laser light and shielding light with the same wavelength as fluorescence. The dichroic mirror 7 has a function of reflecting light with the same wavelength as laser light and transmitting light with the same wavelength as fluorescence. The barrier filter 31 has a function of transmitting light with the same wavelength as fluorescence, and shielding light with other wavelengths (leakage light).

Next, the SLM 13 as a diffraction grating is described.

Figure 2:
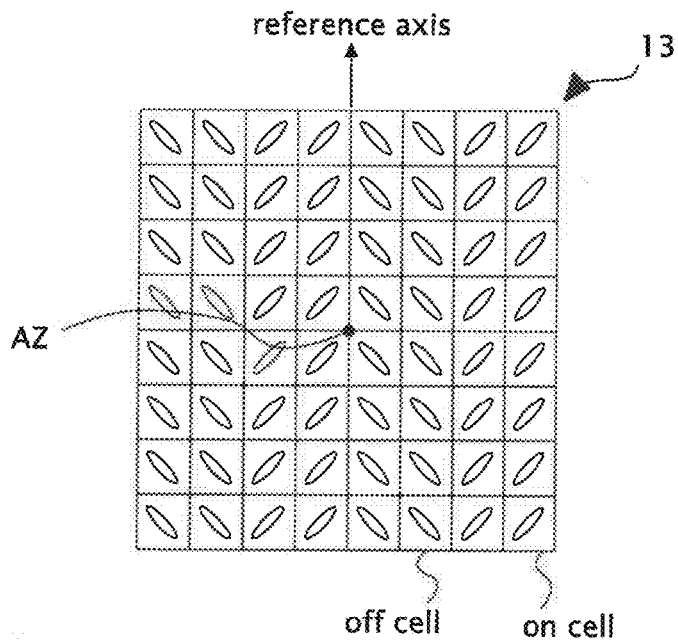
FIG. 2 is a diagram explaining an SLM.

As illustrated in FIG. 2, a lot of reflective liquid crystal cells are two-dimensionally arranged at the SLM 13. FIG. 2 illustrates the smaller number of arrangements of cells than an actual one. The liquid crystal of each cell is, for example, a ferroelectric liquid crystal, and ellipses in FIG. 2 schematically represent liquid crystal molecules seen from a front side of the SLM 13.

When the cell of the SLM 13 is turned on/off, the liquid crystal molecule in the cell rotates around a reference axis. The reference axis is an axis indicating an intermediate direction between a direction of the liquid crystal molecule in a turned-on cell (FIG. 3A) and a direction of the liquid crystal molecule in a turned-off cell (FIG. 3B).

Figures 3A, 3B:
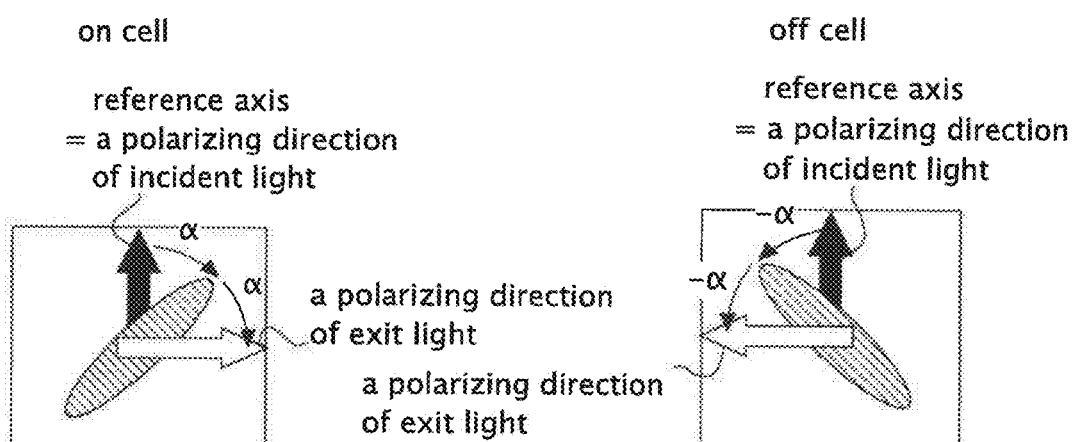
FIG. 3A is a diagram explaining a turned-on cell.
FIG. 3B is a diagram explaining a turned-off cell.

The direction of the liquid crystal molecule in the turned-on cell (a longitudinal direction of the ellipse) rotates by an angle α from the reference axis as illustrated in FIG. 3A. On the other hand, the direction of the liquid crystal molecule in the turned-off cell rotates by an angle −α from the reference axis as illustrated in FIG. 3B. This angle α is an angle uniquely determined depending on a kind of the liquid crystal.

Each of the turned-on cell and the turned-off cell has the same function as a ½-wavelength plate whose fast axis faces the same direction as the liquid crystal molecule in the cell. The fast axis of the ½-wavelength plate is an axis indicating a polarizing direction of incident light where a phase delay amount becomes minimum.

Accordingly, the SLM 13 can be used as a one-dimensional diffraction grating by displaying a pattern where the turned-on cells and the turned-off cells are each periodically arranged in one direction as illustrated in FIG. 2, that is a one-dimensional grating pattern on the SLM 13.

Here, the polarizing direction of the incident light with respect to the SLM 13 is assumed to coincide with the reference axis of the SLM 13. In this case, the SLM 13 functions as a "phase diffraction grating with a phase difference of 4α".

For example, when the angle α is 45°, the turned-on cell rotates the polarizing direction of the incident light by 2×α=+90°, and the turned-off cell rotates the polarizing direction of the incident light by 2×(−α)=−90°. Accordingly, a difference between the phase delay amount imparted on the incident light by the turned-on cell and the phase delay amount imparted on the incident light by the turned-off cell becomes 4α=180°=πrad. In this case, the SLM 13 functions as a "phase diffraction grating with a phase difference of π".

Since the SLM 13 constituted as above sets intensity of the 0th-order diffractive light flux to zero, it is suitable for the 2D-SIM1 which does not need the 0th-order diffractive light flux.

Next, the driver 13A of the SLM 13 is described.

The driver 13A switches the grating pattern displayed on the SLM 13 as described below by turning on/off individual cells arranged at the SLM 13.

For example, the driver 13A switches the spatial frequency of the interference fringe by switching a grating pitch of the grating pattern displayed on the SLM 13.

The driver 13A switches a direction of the interference fringe by switching a direction of the grating pattern displayed on the SLM 13.

The driver 13A shifts a phase of the interference fringe by shifting a phase of the grating pattern displayed on the SLM 13.

In the above description, the angle α unique to the liquid crystal of the SLM 13 is set to 45°, but the angle α unique to the liquid crystal may be set to less than 45°. When the angle α is less than 45°, the intensity of the 0th-order diffractive light flux generated at the SLM 13 does not become zero, but other points are the same as the case when the angle α is 45°.

Next, the beam selecting part 100 illustrated in FIG. 1 is described. The beam selecting part 100 has a function of selecting the light fluxes to be incident on the observational object plane P and a function of maintaining polarized states of the ±first-order diffractive light fluxes incident on the observational object plane P as S-polarization. It is necessary to make the polarizing direction of the ±first-order diffractive light fluxes directed to the observational object plane P orthogonal to a branching direction of the ±first-order diffractive light fluxes in order to make the ±first-order diffractive light fluxes incident on the observational object plane P into the S-polarization.

In this embodiment, the direction of the grating pattern of the SLM 13 is switched in order to switch the direction of the interference fringe. At this time, the branching direction of the ±first-order diffractive light fluxes is also switched. Accordingly, the beam selecting part 100 needs to correspond to this switching.

Figure 4:
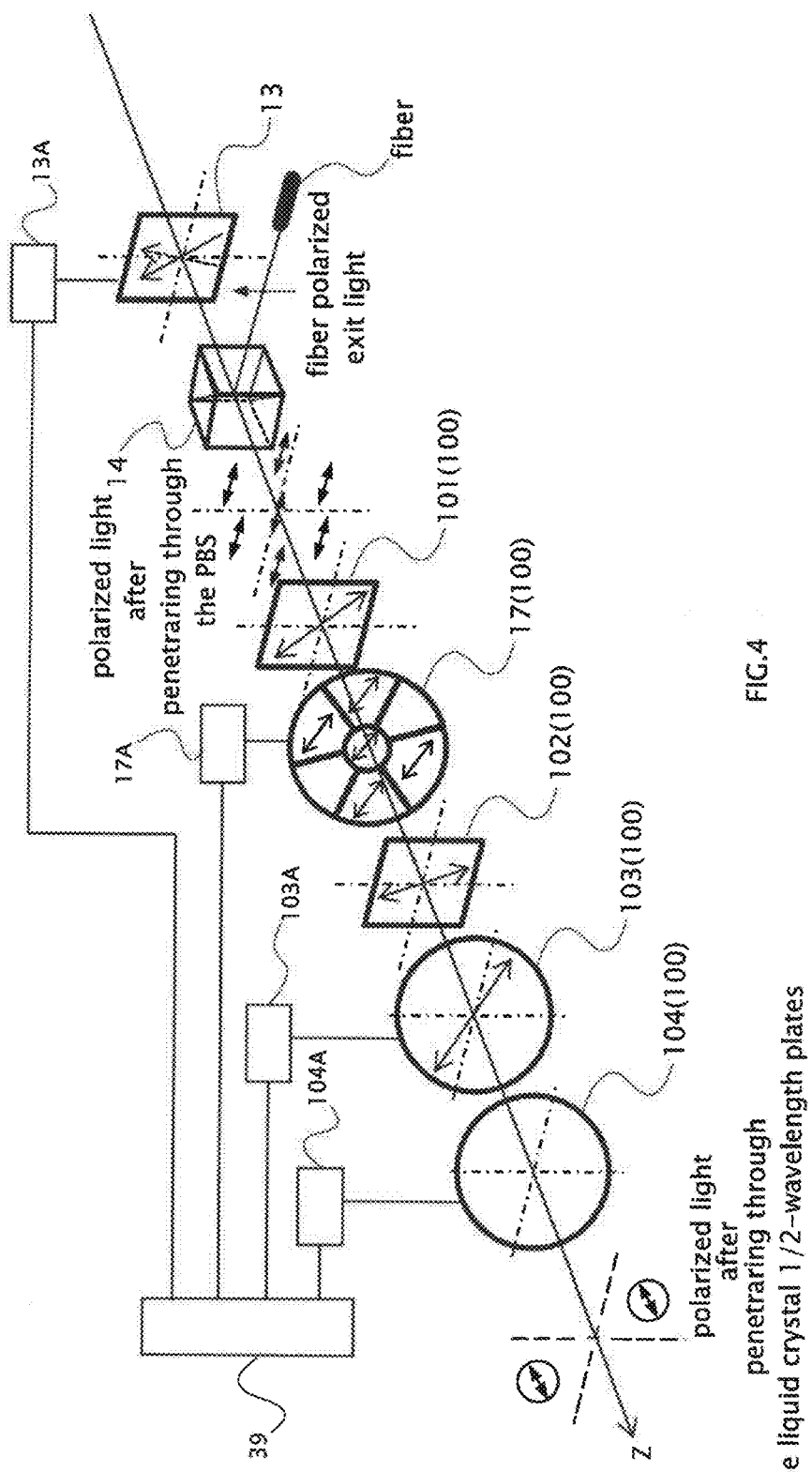
FIG. 4 is a diagram illustrating a configuration example of a beam selecting part.

FIG. 4 is a diagram illustrating a configuration example of the beam selecting part 100. In FIG. 4, though the SLM 13 and the PBS 14 are each illustrated on an incident side of the beam selecting part 100, the collecting lens 16 disposed on the incident side of the beam selecting part 100 is not illustrated.

The beam selecting part 100 includes a ½-wavelength plate 101, a segment wavelength plate 17, a fixed polarizing plate 102, and liquid crystal ½-wavelength plates 103, 104 from the incident side in sequence.

The ½-wavelength plate 101 is disposed such that the fast axis faces a direction rotated by 37.5° from the horizontal when it is seen from a traveling direction of light.

The segment wavelength plate 17 is, for example, a transmissive liquid crystal SLM. The segment wavelength plate 17 is assumed to be the transmissive liquid crystal SLM, and it is called an "SLM 17". A driver 17A being a liquid crystal drive circuit is connected to the SLM 17.

The SLM 17 is the transmissive liquid crystal SLM, and includes a plurality of cells which are each able to be on/off controlled by the driver 17A. For example, the SLM 17 includes a circular cell disposed at a center part, and six cells which are disposed at an outer periphery of the circular cell and formed by dividing a ring-shaped area in a circumferential direction. The driver 17A of the SLM 17 is able to control whether each cell of the SLM 17 functions as the ½-wavelength plate in a direction of the fast axis set in advance depending on a value of a drive signal to be supplied to each cell.

The cell in on-state in the SLM 17 functions as the ½-wavelength plate where the fast axis forms 30° from the horizontal when it is seen from a traveling direction of light. The cell in off-state in the SLM 17 does not have a polarization control function, and light penetrates therethrough while keeping the polarized state when the light was incident.

The fixed polarizing plate 102 is disposed such that the polarizing direction forms 75° from the horizontal when it is seen from the traveling direction of light.

The liquid crystal ½-wavelength plate 103 is on/off controlled by a driver 103A being a liquid crystal drive circuit. When the liquid crystal ½-wavelength plate 103 is in on-state, it functions as the ½-wavelength plate where the fast axis is set in a direction rotated by 15° from the horizontal when it is seen from the traveling direction of light. When the liquid crystal ½-wavelength plate 103 is in off-state, it does not have the polarization control function, and light penetrates therethrough while maintaining the polarized state when the light was incident.

The liquid crystal ½-wavelength plate 104 is on/off controlled by a driver 104A being a liquid crystal drive circuit. When the liquid crystal ½-wavelength plate 104 is in on-state, it functions as the ½-wavelength plate where the fast axis is set in a direction rotated by 45° from the horizontal when it is seen from the traveling direction of light. When the liquid crystal ½-wavelength plate 104 is in off-state, the polarization control function is not held, and light penetrates therethrough while maintaining the polarized state when the light was incident.

Note that the controlling device 39 controls each of the drivers 17A, 103A and 104A.

FIGS. 5A to 5E are diagrams each illustrating a polarized state in each of components illustrated in FIG. 4. FIG. 4 and FIGS. 5A to 5E each illustrate the polarized state when a structured illumination is 45° as an example.

Arrows whose arrowheads are painted in black out of arrows supplied to respective components in FIG. 4 and FIGS. 5A to 5E each indicate a polarizing direction of light which is incident and exits on/from each component. Arrows whose arrowheads are not painted in FIG. 4 and FIGS. 5A to 5E each indicate an axial direction of an element. Since each component is schematically illustrated in FIG. 4 and FIGS. 5A to 5E, it is not necessarily the same as actual one.

First, the polarizing direction of the ±first-order diffractive light fluxes exited from the PBS 14 is constant regardless of the switching of the branching direction of the ±first-order diffractive light fluxes because it is the polarizing direction of light capable of penetrating through a polarization separation plane of the PBS 14.

Figure 5A:
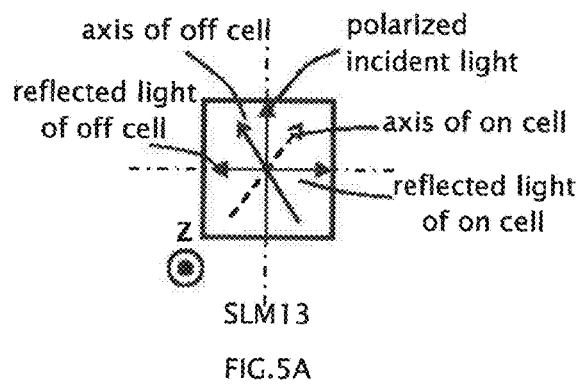
FIG. 5A is a diagram illustrating a polarizing state in components illustrated in FIG. 4.
Figure 5B:
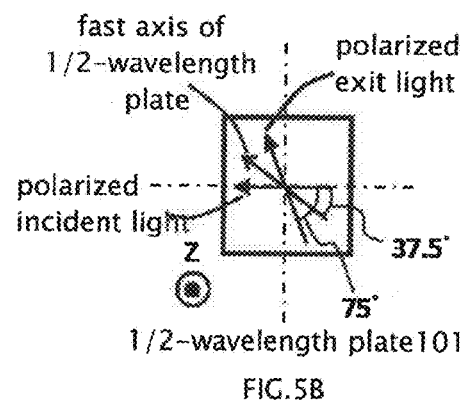
FIG. 5B is a diagram illustrating a rotation of a polarizing direction in a predetermined direction by a fixed ½-wavelength plate.

When the branching direction of the ±first-order diffractive light fluxes is 45°, the beam selecting part 100 needs to convert the polarizing direction of the incident ±first-order diffractive light fluxes into a direction orthogonal to 45° being the branching direction (linearly polarized light at −45°). The polarizing direction is therefore firstly rotated in a predetermined direction by the fixed ½-wavelength plate 101. Here, the polarizing direction after passing through the PBS 14 is set to 0° in horizontal, and the fast axis of the ½-wavelength plate 101 is disposed in a direction rotated by 37.5° from the horizontal when it is seen from the traveling direction of light. It is thereby possible to rotate the polarizing direction by 75° from the horizontal (FIG. 5B).

Figure 5C:
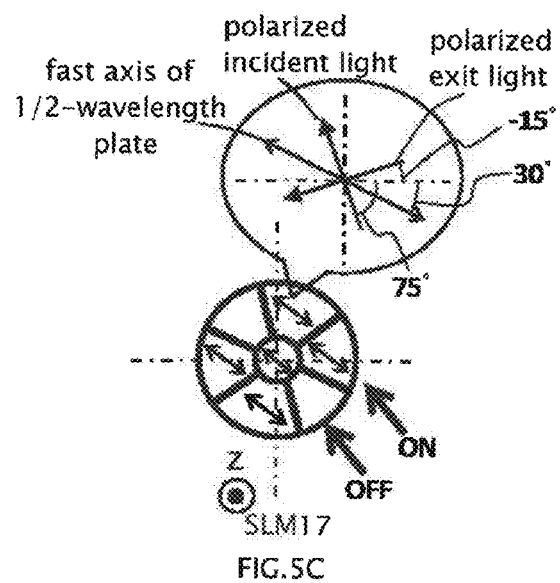
FIG. 5C is a diagram illustrating cells, among cells of the SLM, in which ±first-order diffractive light fluxes with the branching direction of 45° incident as off-cells, and other cells as on-cells.
Figure 5D:
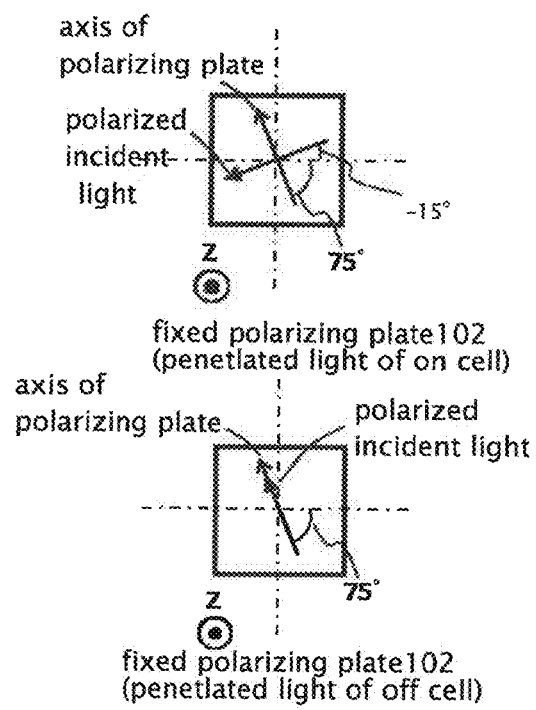
FIG. 5D is a diagram illustrating light which penetrates through the SLM incident on a fixed polarizing plate.

Subsequently, the controlling device 39 controls to turn off the cells where the ±first-order diffractive light fluxes with the branching direction of 45° are incident, and turn on the other cells out of the cells of the SLM 17 through the driver 17A. The on-cells of the SLM 17 function as the ½-wavelength plate whose fast axis is set in a direction rotated by 30° from the horizontal when it is seen from the traveling direction of light, and the off-cells of the SLM 17 do not have the polarization control function, and light penetrates therethrough while keeping the polarized state when the light was incident. As a result, the polarized states after passing through the SLM 17 are as follows: light passing through areas where the ±first-order diffractive light fluxes with the branching direction of 45° are incident (the off-cells of the SLM 17) stays the linearly polarized light at 75° from the horizontal when it is seen from the traveling direction of light; and light passing through the other areas (the on-cells of the SLM 17) is converted into the linearly polarized light at −15° from the horizontal when it is seen from the traveling direction of light (FIG. 5C).

The light which penetrates through the SLM 17 is incident on the fixed polarizing plate 102. At this time, since the light passing through the on-cells of the SLM 17 is converted into the linearly polarized light at −15° from the horizontal when it is seen from the traveling direction of light, the light is shielded by the fixed polarizing plate 102 having the polarizing direction at 75° (upper stage in FIG. 5D). Meanwhile, since the light passing through the off-cells of the SLM 17 is the linearly polarized light at 75° from the horizontal when it is seen from the traveling direction of light, the light penetrates through the fixed polarizing plate 102 having the polarizing direction at 75° as it is (lower stage in FIG. 5D).

The controlling device 39 controls to turn on the liquid crystal ½-wavelength plate 103 through the driver 103A. Besides, the controlling device 39 controls to turn off the liquid crystal ½-wavelength plate 104 through the driver 104A.

Figure 5E:
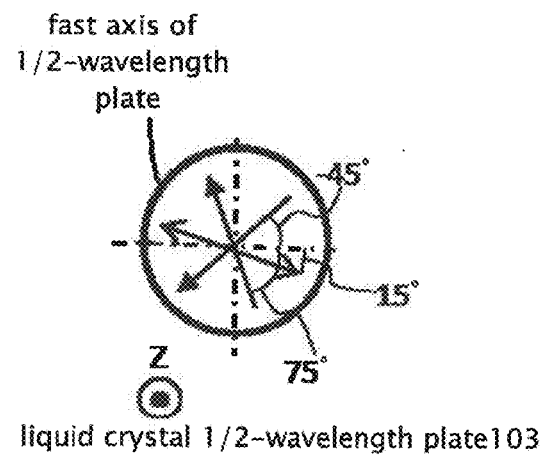
FIG. 5E is a diagram illustrating the ±first-order diffractive light fluxes with the branching direction of 45° converted into linearly polarized light at −45° from a horizontal seen from a traveling direction of light by a liquid crystal ½-wavelength plate having a fast axis at 15°.

The liquid crystal ½-wavelength plate 103 functions as the ½-wavelength plate whose fast axis is set in a direction rotated by 15° from the horizontal when it is seen from the traveling direction of light by being turned on. Though the ±first-order diffractive light fluxes with the branching direction of 45° which pass through the off-cells of the SLM 17 are linearly polarized light at 75° from the horizontal when it is seen from the traveling direction of light, the liquid crystal ½-wavelength plate 103 having the fast axis at 15° converts into the linearly polarized light at −45° from the horizontal when it is seen from the traveling direction of light (FIG. 5E). Since the liquid crystal ½-wavelength plate 104 is turned off, the light penetrates through the liquid crystal ½-wavelength plate 104 while keeping its polarizing state. As described above, the ±first-order diffractive light fluxes exited from the PBS 14 pass through the beam selecting part 100, and then are converted into the polarizing state of −45° orthogonal to the branching direction of 45°.

The controlling device 39 may appropriately switch the on/off states of the cells of the SLM 17, the on/off states of the liquid crystal ½-wavelength plate 103 and the on/off states of the liquid crystal ½-wavelength plate 104 in order to change the branching direction of the ±first-order diffractive light fluxes in the beam selecting part 100.

Figure 6A:
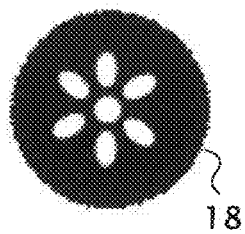
Figure 6B:
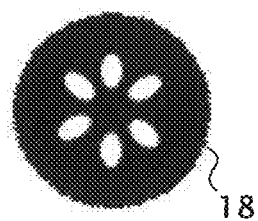

In the beam selecting part 100 illustrated in FIG. 4, a mask 18 including openings corresponding to the respective cells of the SLM 17 may be inserted into an optical path of the beam selecting part 100 in order to suppress passage of noise diffraction light which is generated due to a pixel structure or the like of the SLM 13. The mask 18 is, for example, a black thin mask substrate where opening parts (holes) are formed only at incident areas of necessary diffraction light. Otherwise, the mask 18 may be, for example, a liquid crystal element where transmissive cells are disposed at the incident areas of the necessary diffraction light, and opaque cells are disposed at incident areas of unnecessary diffraction light. FIGS. 6A and 6B are diagrams each illustrating an example of the mask 18 which is inserted into the beam selecting part 100. For example, FIG. 6A illustrates a pattern example of a three-beam mask 18 which allows the 0th-order diffractive light flux and the ±first-order diffractive light fluxes to pass through as described later, and FIG. 6B illustrates a pattern example of a two-beam mask 18 which allows the ±first-order diffractive light fluxes to pass through. Note that in FIGS. 6A and 6B, a black part of the mask 18 represents a light-shielding area.

Next, depth adjustment of the observational object plane P is described.

Normally, the super-resolution effect of the 2D-SIM1 increases as the spatial frequency of the interference fringe is higher. The spatial frequency of the interference fringe in a conventional 2D-SIM has been therefore set near an upper limit value of the transmittable spatial frequency by the objective lens 6 (an optical cutoff frequency). However, the following two problems mainly occur when the depth of the observational object plane P is adjusted.

Figure 7B:
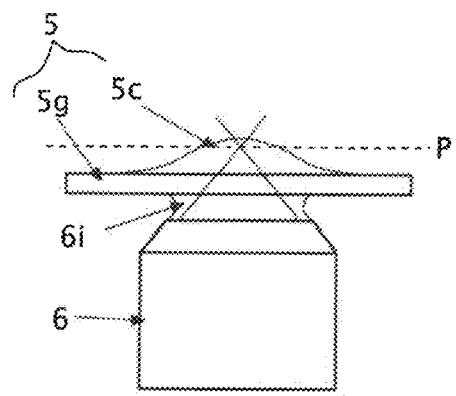
FIG. 7B is a diagram explaining a relationship between the objective lens and the specimen during a deep part observation time.

A first problem is as follows. That is, when the observational object plane P positions directly above the cover glass 5g (a surface observation time) as illustrated in FIG. 7A, an aberration of the objective lens 6 can be ignored, but when the observational object plane P positions at a deep part of the culture fluid 5c (a deep part observation time) as illustrated in FIG. 7B, the aberration of the objective lens 6 cannot be ignored. When a combination of a thickness and a refractive index of a medium existing in an optical path from the tip of the objective lens 6 to the observational object plane P becomes an unexpected state (index mismatch) such as the deep part observation (FIG. 7B), a spherical aberration of the objective lens 6 cannot be suppressed because the objective lens 6 is designed for the surface observation (FIG. 7A).

Accordingly, when the deep part is observed (FIG. 7B), an MTF (modulation transfer function) of the image-forming optical system 30 including the objective lens 6 deteriorates, a contrast of an image formed on the imaging plane 36 by the image-forming optical system 30 is lowered, and image quality of an restoration image consequently deteriorates.

A second problem is as follows. That is, when the deep part is observed (FIG. 7B), scattered light generated by various kinds of structures such as cells existing on a non-observational object plane is incident on the objective lens 6 as noise light, and may finally reach the imaging sensor 35.

An SN ratio of the imaging sensor 35 therefore deteriorates when the deep part is observed (FIG. 7B).

Accordingly, the upper limit value of the spatial frequency which can be imaged by the imaging sensor 35 (a substantial cutoff frequency) is lowered when the deep part is observed (FIG. 7B) resulting from the first problem (the problem in which the image quality of the super-resolved image deteriorates due to the lowering of the contrast of the image) and the second problem (the deterioration of the SN ratio).

In this embodiment, the first problem (the problem in which the image quality of the super-resolved image deteriorates due to the lowering of the contrast) is to be solved, mainly. Incidentally, both of the first problem (the problem in which the image quality of the super-resolved image deteriorates due to the lowering of the contrast) and the second problem (the deterioration of the SN ratio) are to be solved in a later-described second and third embodiment.

Hereinafter, the first problem (the problem in which the image quality of the super-resolved image deteriorates due to the lowering of the contrast) and a countermeasure thereof in this embodiment are described.

Figure 8:
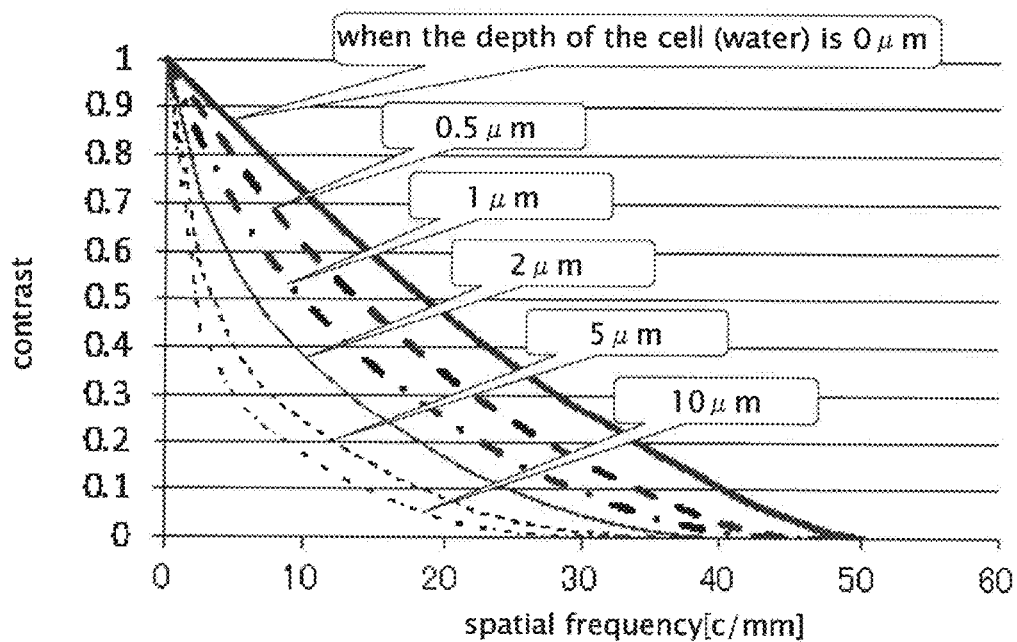
FIG. 8 is a diagram illustrating an MTF of an image-forming optical system by each depth of an observational object plane.

FIG. 8 is a diagram illustrating the MTF (modulation transfer function) of the image-forming optical system 30 by each depth of the observational object plane P. A horizontal axis in FIG. 8 is the spatial frequency of the image formed on the imaging plane 36 by the image-forming optical system 30, and a vertical axis in FIG. 8 is a contrast of the image formed on the imaging plane 36 by the image-forming optical system 30.

Here, the depth of the observational object plane P when the surface is observed is set to "0" (zero) [μm], the immersion liquid 61 is set to oil, the culture fluid 5c containing cells is regarded as water, a magnification of the objective lens 6 is assumed to be 100 times, a numerical aperture NA of the objective lens 6 is assumed to be 1.49, a use wavelength 1 of the image-forming optical system 30 is assumed to be 0.587 [μm], and an image-forming magnification M of the image-forming optical system 30 is assumed to be 100 times.

As illustrated in FIG. 8, when the depth of the observational object plane P (the depth of the cell (water)) is "0" (zero) [μm], a transmittable maximum spatial frequency is 50.7 [c/mm] because the image-forming optical system 30 is able to transmit up to the cutoff frequency. This cutoff frequency R is represented by an expression of $R=1000/(\lambda/(2(NA/M)))$.

However, when the depth of the observational object plane P becomes larger than zero, a shape of an MTF curve of the image-forming optical system 30 changes as illustrated in FIG. 8 to lower the contrast of the image, and thereby, the transmittable maximum spatial frequency is lowered in the image-forming optical system 30. For example, when the depth of the observational object plane P is 10 [μm], the transmittable maximum spatial frequency of the image-forming optical system 30 is lowered to approximately 30 [c/mm].

If the spatial frequency of the interference fringe is fixed to a value which is the same as the cutoff frequency R=50.7 [c/mm] when the depth of the observational object plane P is zero, the transmittable spatial frequency is lowered when the depth of the observational object plane P is made large, and a phenomenon in which the interference fringe pattern cannot be transmitted to the imaging plane 36 side occurs. When restoration processing of an image is performed, information of the spatial frequency of a structured illumination is required, and therefore, the information of the spatial frequency of the structured illumination is necessary to be read out of an acquired image. Accordingly, when the phenomenon in which the interference fringe pattern cannot be transmitted to the imaging plane 36 side occurs, the information of the spatial frequency of the structured illumination cannot be correctly read out of the acquired image, a restoration processing calculation is performed while noises are misjudged as the information, and the image quality of the super-resolved image deteriorates.

In this embodiment, the spatial frequency of the interference fringe is controlled in order to solve the first problem (the problem in which the image quality of the super-resolved image deteriorates due to the lowering of the contrast).

Concretely, in this embodiment, the spatial frequency of the interference fringe is controlled such that the contrast of the interference fringe projected on the imaging plane 36 becomes a certain level or more even when the depth of the observational object plane P is switched in a predetermined range. It is thereby possible to prevent the deterioration of the image quality of the super-resolved image.

Further, in this embodiment, the spatial frequency of the interference fringe is controlled such that the contrast of the interference fringe projected on the imaging plane 36 falls within a proper range even when the depth of the observational object plane P is switched in the predetermined range. It is thereby possible to keep the image quality of the super-resolved image.

FIG. 9 is a diagram illustrating a relationship between the depth of the observational object plane P and a proper value of the spatial frequency of the interference fringe. Here, the spatial frequency of the interference fringe is converted into a value at the imaging plane 36. Besides, a depth range of the observational object plane P is assumed to be "0" (zero) to 10 [μm] so that a whole of cultured cells can be completely covered.

As illustrated in FIG. 9, the proper value of the spatial frequency of the interference fringe becomes lower as the depth of the observational object plane P becomes larger.

Concretely, in this embodiment, the proper value of the spatial frequency of the interference fringe is set to 40 [c/mm] when the depth of the observational object plane P is "0" (zero) [μm] or more and less than 0.5 [μm].

The proper value of the spatial frequency of the interference fringe is set to 35 [c/mm] when the depth of the observational object plane P is 0.5 [μm] or more and less than 1 [μm].

The proper value of the spatial frequency of the interference fringe is set to 30 [c/mm] when the depth of the observational object plane P is 1 [μm] or more and less than 2 [μm].

The proper value of the spatial frequency of the interference fringe is set to 25 [c/mm] when the depth of the observational object plane P is 2 [μm] or more and less than 5 [μm].

The proper value of the spatial frequency of the interference fringe is set to 20 [c/mm] when the depth of the observational object plane P is 5 [μm] or more and less than 10 [μm].

According to these proper values, the contrast of the interference fringe falls within a range of 0.03 to 0.1 even when the depth of the observational object plane P is switched within the range of "0" (zero) [μm] to 10 [μm].

In this embodiment, since the spatial frequency of the interference fringe is intentionally set to be low so that the image-forming optical system 30 is able to accurately transmit the interference fringe pattern, the super-resolution effect is lowered to that extent. Values illustrated in a bottom row in FIG. 9 are each a super-resolution effect E. The super-resolution effect a is represented by the spatial frequency K of the interference fringe and the cutoff frequency R of the image-forming optical system 30 when the depth of the observational object plane P is zero as ε=(R+K)/R.

It can be seen from the bottom row in FIG. 9 that the super-resolution effect falls within a good range of 1.4 to 1.8 even when the depth of the observational object plane P is switched within the range of 0 to 10 [μm] in this embodiment.

Though the combination of the immersion liquid (oil) 6i and the culture fluid (water) 5c is assumed as the media existing above and below the cover glass 5g in the above description, other combinations can be used. For example, a mounting medium can be used instead of water.

For example, when ProlongGold (Prolong is a registered trademark) being a general-purpose mounting medium is used, the relationship between the depth of the observational object plane P and the proper value of the spatial frequency of the interference fringe is as illustrated in FIG. 10.

Data in FIG. 10 correspond to ones where the depths of water of data in FIG. 9 are converted into depths of the mounting medium. This conversion is based on the following relational expression.

$$tb=(no-nw)/(no-nb) \times tw$$

Here, "tw" is the depth of water, "tb" is the depth of the mounting medium, "nw" is a refractive index of water, "nb" is a refractive index of the mounting medium, and "no" is a refractive index of the immersion liquid (oil).

Since the refractive index "no" of oil is 1.51, the refractive index "nw" of water is 1.33, and the refractive index "nb" of the mounting medium (ProlongGold) is 1.46, it can be seen that a ratio between the depth of water "tw" and the depth of the mounting medium "tb" is 10:36 according to the above relational expression. In this case, a maximum mounting medium depth corresponding to a maximum water depth of 10 [μm] is 36 [μm].

Accordingly, a depth range of the observational object plane P can be set to "0" (zero) to 36 μm when the mounting medium is used where the depth range of the observational object plane P is "0" (zero) to 10 μm when water is used.

A tissue section cell having a relatively large thickness can be covered by the wide depth range of "0" (zero) to 36 μm as above. That is, application of the 2D-SIM1 spreads if the mounting medium is used instead of water.

Next, an operation flow of the 2D-SIM1 is described. Here, the data illustrated in FIG. 9 and the data illustrated in FIG. 10 are assumed to be stored in the controlling device 39 as, for example, look-up tables.

Figure 11:
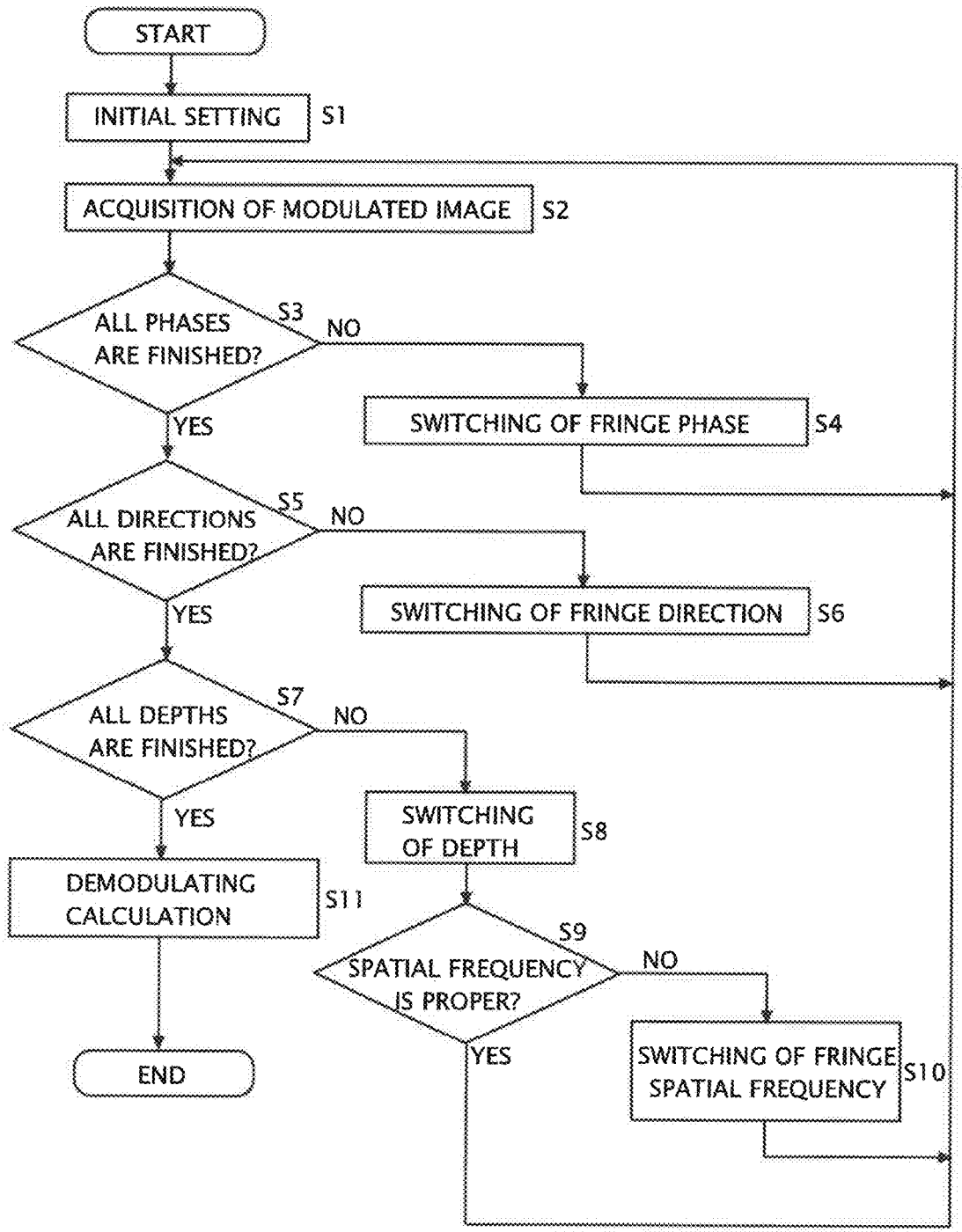
FIG. 11 is an operation flowchart of the 2D-SIM.

FIG. 11 is an operation flowchart of the 2D-SIM1. Hereinafter, each step in FIG. 11 is described in sequence.

Step S1: The controlling device 39 sets a direction of the interference fringe, a phase of the interference fringe, and a spatial frequency of the interference fringe to initial values through the driver 13A. The controlling device 39 sets a depth the observational object plane to an initial value through the stage 50. The initial value of the spatial frequency of the interference fringe is 40 [c/mm], and the initial value of the depth is "0" (zero) [μm]

Step S2: The controlling device 39 acquires a modulated image which is an image of a specimen modulated by the interference fringe by driving a not-illustrated coherent light source and the imaging sensor 35, and sends out the modulated image to the image storing-calculating device 40.

Step S3: The controlling device 39 determines whether the number of phases of the interference fringe reaches a required number, then transfers to Step S4 when it is not reached, and transfers to Step S5 when it is reached.

Step S4: The controlling device 39 shifts a phase of a grating pattern displayed on the SLM 13 for only one step through the driver 13A, and returns to Step S2. The phase of the interference fringe shifts for only one step according to this step.

Step S5: The controlling device 39 determines whether the number of directions of the interference fringe reaches a required number, then transfers to Step S6 when it is not reached, and transfers to Step S7 when it is reached.

Step S6: The controlling device 39 switches a direction of the grating pattern displayed on the SLM 13 for only one step through the driver 13A, and returns to Step S2.

The direction of the interference fringe is switched for only one step according to this step.

Step S7: The controlling device 39 determines whether the number of depths of the observational object plane reaches a required number, then transfers to Step S8 when it is not reached, and transfers to Step S11 when it is reached.

Step S8: The controlling device 39 approximates the specimen 5 to the objective lens 6 side for only one step through the stage 50, and transfers to Step S9. The depth of the observational object plane increases for only one step according to this step.

Step S9: The controlling device 39 refers to the look-up table, determines whether the current spatial frequency of the interference fringe is proper, then returns to Step S2 when it is proper, and transfers to Step S10 when it is not proper. Note that the controlling device 39 in this step refers to the look-up table in FIG. 9 when water is used as the medium existing on the cover glass 5g, and refers to the look-up table in FIG. 10 when the mounting medium is used. Note that it is assumed that a kind of the medium existing on the cover glass 5g is previously specified from a user to the controlling device 39.

Step S10: The controlling device 39 switches a grating pitch of the grating pattern displayed on the SLM 13 through the driver 13A, and returns to Step S2. The spatial frequency of the interference fringe is switched to the proper value according to this step.

Step S11: The image storing-calculating device 40 groups a plurality pieces of modulated images acquired in Steps S1 to S10 depending on the spatial frequency of the interference fringe or the depth of the observational object plane. At least one of "the phase of the inference fringe", "the direction of the interference fringe", "the depth of the observational object plane", and "the spatial frequency of the interference fringe" is different among the plurality pieces of modulated images. The image storing-calculating device 40 finds the super-resolved image of the specimen 5 by performing a publicly-known demodulating calculation by each group. A demodulating calculation described in Specification of U.S. Pat. No. 8,115,806, a demodulating calculation described in a thesis of Heintzmann and so on (described below) (Slice3D algorism), and so on can be applied to this demodulating calculation. The Slice3D algorism of Heintzmann and so on is suitable for individually demodulating a plurality of modulated images having different spatial frequencies of the interference fringe.

The thesis of Heintzmann and so on: "Phase optimization for structured illumination microscopy", KaiWicker, OndreJ Mandula, Gerrit Best, Reto Fiolka, and Rainer Heintzmann Received 28 Sep. 2012; revised 6 Jan. 2013; accepted 7 Jan. 2013; published 18 Jan. 2013(C) 2013 OSA 28 January 2013/Vol. 21, No. 2/OPTICS EXPRESS 2033

Next, the first problem (the problem in which the image quality of the super-resolved image deteriorates due to the lowering of the contrast) and the countermeasure thereof in this embodiment are described from another viewpoint.

In FIG. 8, it is described that the first problem (the problem in which the image quality of the super-resolved image deteriorates due to the lowering of the contrast) occurs when the information of the spatial frequency of the structured illumination is read out of the acquired images and demodulation processing is performed, and the countermeasure thereof is described.

Though the demodulation processing can be performed by setting the spatial frequency of the structured illumination as a known value without reading the information of the spatial frequency of the structured illumination out of the acquired images, the first problem (the problem in which the image quality of the super-resolved image deteriorates due to the lowering of the contrast) occurs also in this case.

Hereinafter, it is described that the first problem (the problem in which the image quality of the super-resolved image deteriorates due to the lowering of the contrast) can be solved by a method of this embodiment even in the case when demodulation processing is performed while setting the spatial frequency of the structured illumination as the known value, with reference to FIG. 12 and FIG. 13.

Figure 12:
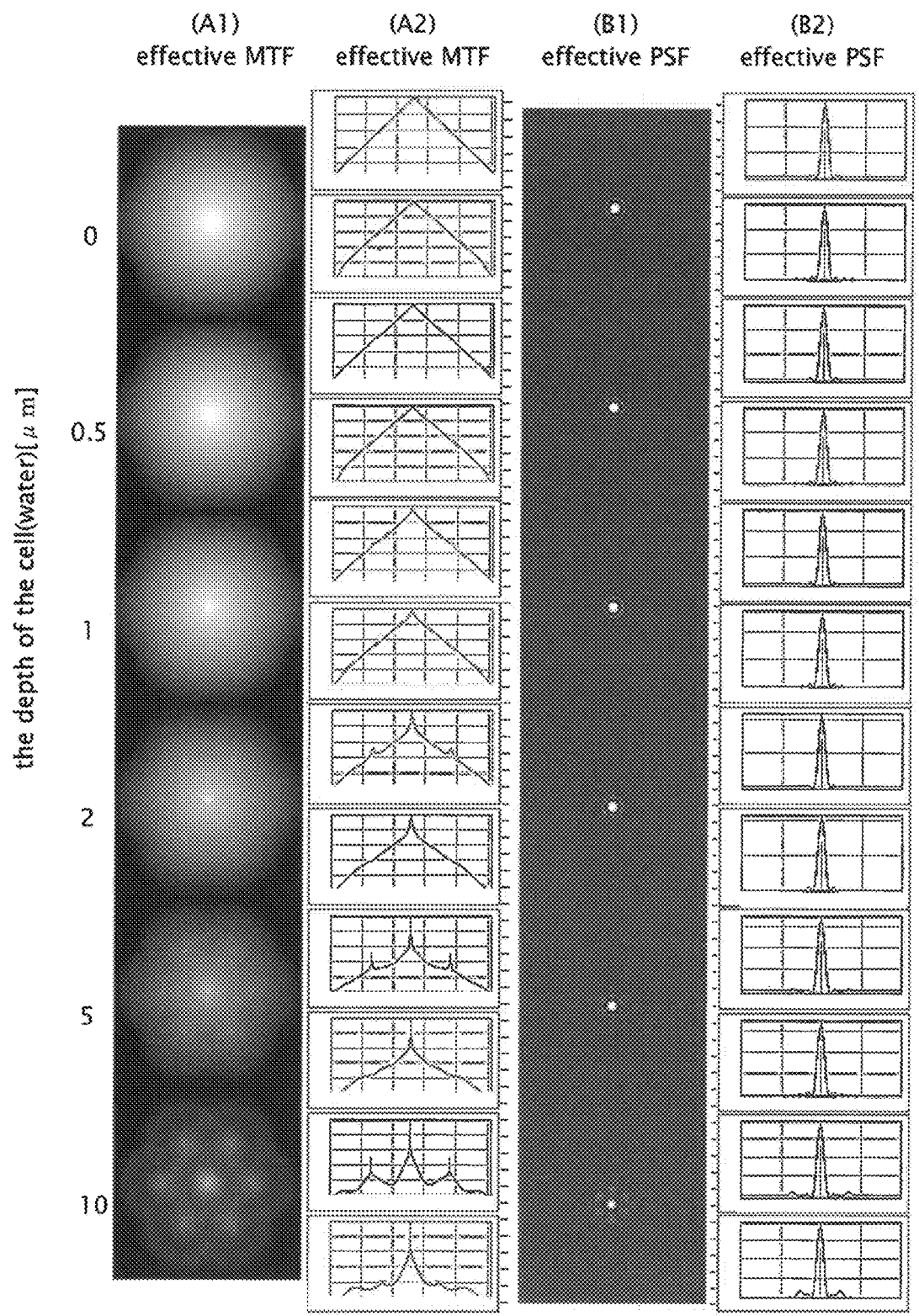
FIG. 12 is a diagram illustrating performance of a 2D-SIM in a comparative example.

A left side in FIG. 12 illustrates an effective MTF of a comparative example by each depth of the observational object plane, and a right side in FIG. 12 illustrates an effective PSF (point spread function) of the comparative example by each depth of the observational object plane. The depth of the observational object plane becomes large toward the lower side in FIG. 12.

Here, the effective MTF means a transfer function when the structured illumination is performed under a state where the image-forming optical system 30 has each of the transfer functions illustrated in FIG. 8, and the processing is performed while setting the information of the spatial frequency of the structured illumination as the known value. Besides, the effective PSF means a point image intensity distribution after the structured illumination is performed under the state where the image-forming optical system 30 has each of the transfer functions illustrated in FIG. 8, and the demodulation processing is performed while setting the information of the spatial frequency of the structured illumination as the known value.

The effective MTF illustrated by A1 in FIG. 12 represents an XY plane of a wave number space, and intensity by each frequency is indicated by whiteness of color. A2 represents a profile diagram of the corresponding effective MTF, where the top represents a profile in an X direction, and the bottom represents a profile in a Y direction. A horizontal axis in the profile diagram is the spatial frequency, where a center is "0" (zero), and it becomes higher frequency toward a periphery. A vertical axis represents normalized intensity.

The effective PSF in B1 represents intensity on an XY plane of a real space, and intensity at a position is indicated by whiteness of color. B2 represents a profile diagram of the corresponding effective PSF, where the top is the profile diagram in the X direction, and the bottom is the profile diagram in the Y direction, similarly. A horizontal axis in the profile diagram of the PSF is a position on an image plane, where a center is an image center, and a vertical axis is normalized image intensity.

As illustrated in FIG. 12, a discontinuous peak occurs at a position corresponding to the spatial frequency K of the interference fringe in the wave number space (MTF), and a luminescent point noise occurs at a periphery of a point image in the real space (PSF) in the comparative example.

In the super-resolved image acquired in the comparative example, bordering such as a double image and a six symmetrical noise pattern appear at a periphery of a cellular image.

It can be seen that the first problem (the problem in which the image quality of the restoration image deteriorates due to the lowering of the contrast) occurs in this embodiment even when the demodulation processing is performed while setting the spatial frequency of the structured illumination as the known value.

Since the information of the spatial frequency of the structured illumination is treated as already known in the calculation in FIG. 12, the noise pattern is resulting from only the discontinuous peak, but actually, the problem where the information of the structured illumination cannot be transmitted to the image plane also occurs as examined in FIG. 8. Accordingly, it is thought that the processing cannot be done well, and more severe noise occurs.

Figure 13:
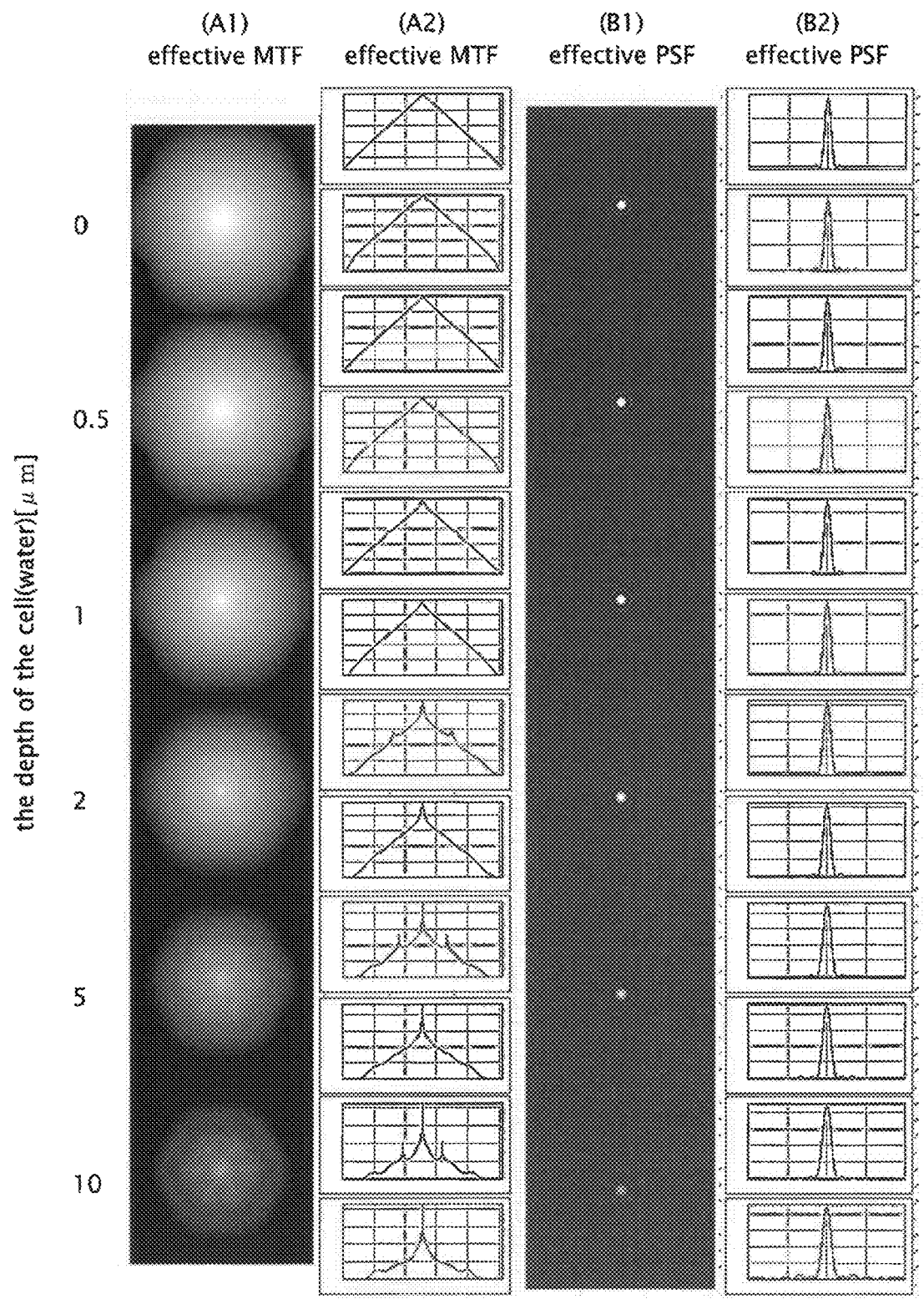
FIG. 13 is a diagram illustrating performance of the 2D-SIM in the present embodiment.

FIG. 13 is a diagram illustrating performance of this embodiment. A notation system of FIG. 13 is the same as the notation system of FIG. 12.

As illustrated in FIG. 13, since the spatial frequency of the interference fringe is controlled in this embodiment, the first problem (a spherical aberration of the objective lens 6) is not outstanding, the discontinuous peak seldom occurs at the position corresponding to the spatial frequency K of the interference fringe in the wave number space (MTF), and the luminescent point noise seldom occurs at the periphery of the point image in the real space (PSF) even if the depth of the observational object plane is large.

Accordingly, in the super-resolved image acquired in this embodiment, bordering such as a double image and a six symmetrical noise pattern do not appear at a periphery of a cellular image.

Next, specifications of the imaging sensor 35 and the SLM 13 are concretely described.

Here, a CMOS imaging sensor with a pixel size of 6.5 μm, and the number of pixels of 1024×1024 [pixel] is assumed to be used as the imaging sensor 35.

As described above, in this embodiment, the spatial frequency of the minutest interference fringe out of the interference fringe to be formed on the imaging plane 36 of the imaging sensor 35 is 40 [c/mm]. When the interference fringe is formed on the imaging plane 36, the number of fringe at a whole of the imaging plane 36 becomes 40 [c/mm]×6.5 [μm]/1000×1024 [pixel]=266 [Hz].

Here, a main pixel interval in a lateral direction of the number of pixels (the number of cells) of a unit cell being a minimum unit of the grating pattern which is to be displayed on a whole of the SLM 13 is assumed to be "9". This unit cell means a group of pixels necessary for displaying the grating pattern for one period on the SLM 13 in a direction displacing the grating pattern in a phase modulation. The whole of the grating pattern can be displayed on the SLM 13 by arranging the unit cells on the SLM 13 with no space.

Figure 23A:
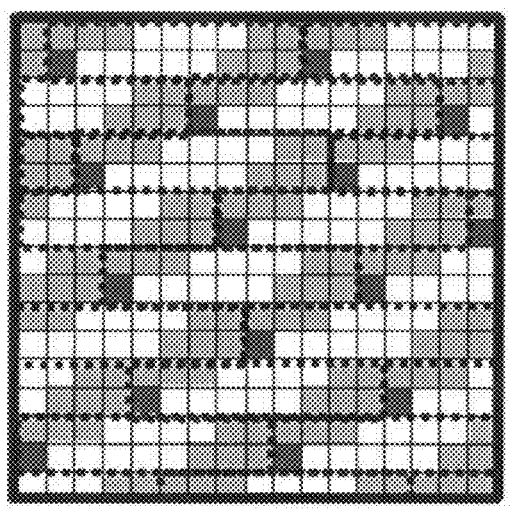
FIG. 23A is a diagram illustrating a part of an SLM.
Figure 23B:
FIG. 23B is a diagram illustrating unit cells of the SLM.

Here, the unit cell is described by using FIGS. 23A and 23B. FIG. 23A illustrates a part of the SLM 13. An area surrounded by a dotted line is the unit cell when the grating pattern is formed as illustrated in this diagram. FIG. 23B is a diagram where only the unit cell is picked up and illustrated. The unit cells illustrated in FIG. 23B are spread all over the SLM 13, then the grating pattern can be expressed. Since the main pixel interval of the unit cell in the lateral direction is "9", a grating period in the lateral direction is 9 [pixel]. There can be enabled a phase modulation where the phase of the structured illumination is shifted every $2\pi/3$ [rad] for three times by displacing the grating pattern on the SLM 13 every 3 [pixel] in the lateral direction.

In this case, the number of pixels (the number of cells) required for all over the SLM 13 is 266 [Hz]/2×9 [pixel]=1198 [pixel].

A reason why 266 [Hz] is divided by "2" is because the number of fringe of the image of the SLM 13 (=the interference fringe) formed by the ±first-order diffractive light fluxes is two times of the number of gratings of the grating pattern displayed on the SLM 13.

Accordingly, the number of pixels (the number of cells) of the SLM 13 is set to be 1198 or more in this embodiment.

Incidentally, since there is an SLM having 1280 [pixel] in general-purpose SLMs, it is possible to surely project the required interference fringe on the imaging plane 36 if the SLM is used as the SLM 13.

In the above description, the grating period of the SLM 13 in the lateral direction which is necessary to form the interference fringe with the spatial frequency of 40 [c/mm] is set to 9 [pixel].

In this case, the grating period of the SLM 13 in the lateral direction which is necessary to form the interference fringe with the spatial frequency of 35 [c/mm] is 10.3 [pixel].

The number of pixels of the unit of the SLM 13 necessary to form the interference fringe with the spatial frequency of 30 [c/mm] is 12 [pixel].

The grating period of the SLM 13 in the lateral direction necessary to form the interference fringe with the spatial frequency of 25 [c/mm] is 14.4 [pixel].

The grating period of the SLM 13 in the lateral direction necessary to form the interference fringe with the spatial frequency of 20 [c/mm] is 18 [pixel].

When the grating period corresponding to the required spatial frequency is not a multiple of three, the grating period may be expanded such that the unit cell can be formed by an integer of multiple of three in a vertical direction or a lateral direction.

Complement of First Embodiment

Figure 14:
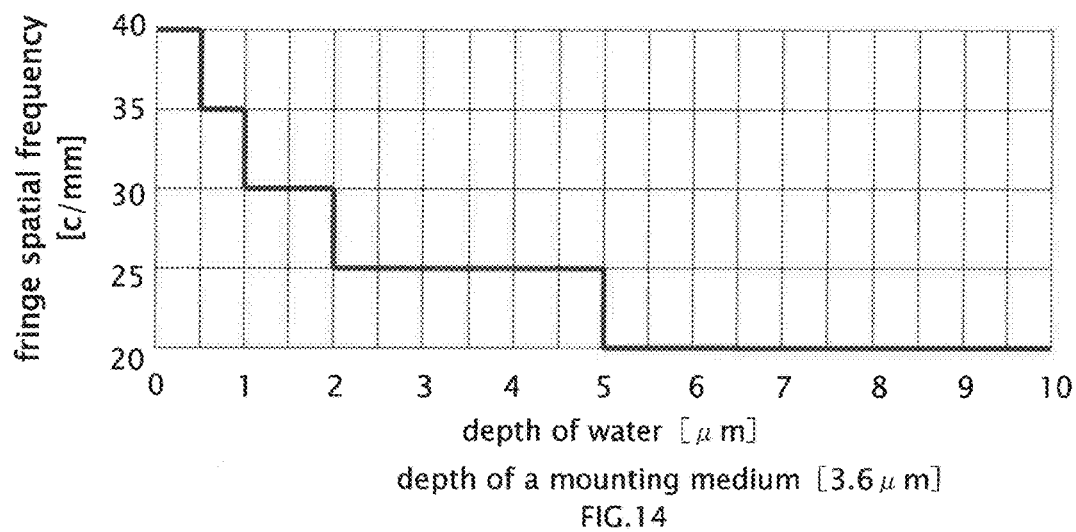
FIG. 14 is a diagram illustrating a change pattern of the spatial frequency of the interference fringe with respect to the depth of the observational object plane.

In the first embodiment, the change pattern of the spatial frequency of the interference fringe with respect to the depth of the observational object plane is the "step state" (refer to FIG. 14), but it may be a further fine step state, or may be a further rough step state.

Figure 15:
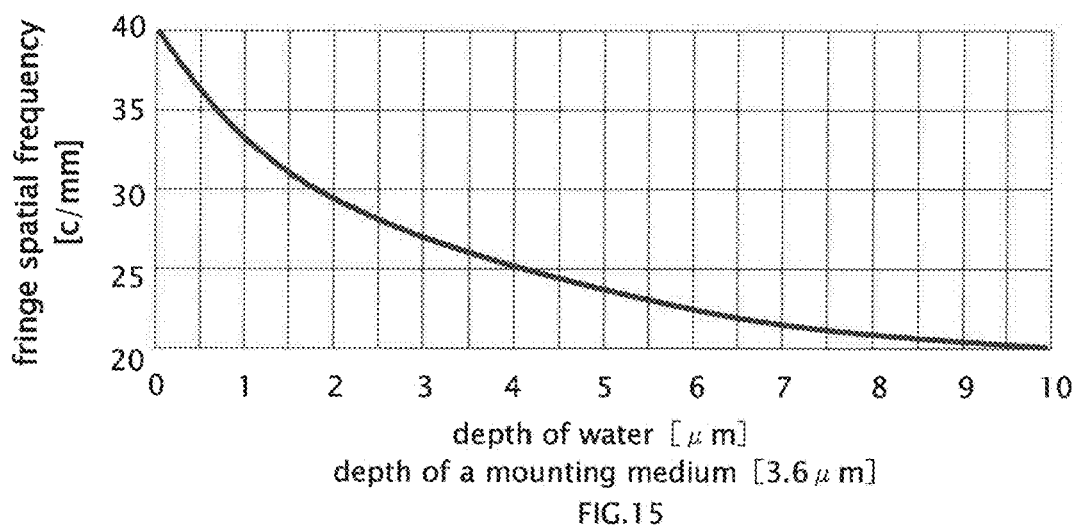
FIG. 15 is a diagram illustrating an example where the change pattern of the spatial frequency of the interference fringe with respect to the depth of the observational object plane is made to be a smooth curved state.
Figure 16:
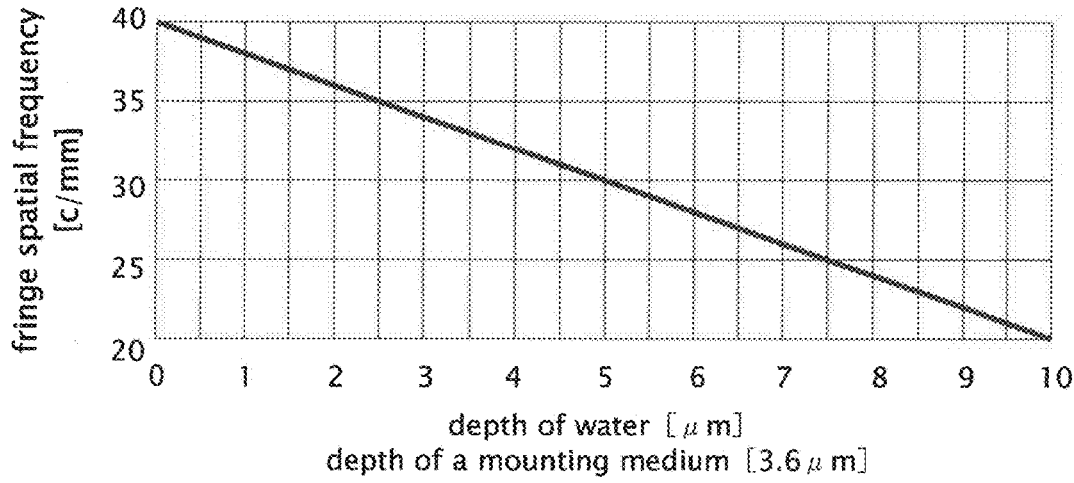
FIG. 16 is a diagram illustrating an example where the change pattern of the spatial frequency of the interference fringe with respect to the depth of the observational object plane is made to be a linear state.

In the first embodiment, the change pattern of the spatial frequency of the interference fringe with respect to the depth of the observational object plane is the "step state" (refer to FIG. 14), but a part or all of the change patterns may be a "a smooth curved state" (refer to FIG. 15), or a part or all of the change patterns may be a "a linear state" (refer to FIG. 16).

In the first embodiment, a ratio of a change amount of the spatial frequency of the interference fringe with respect to a change amount of the depth of the observational object plane is set to be larger as the depth of the observational object plane is smaller (refer to FIG. 14 and FIG. 15), but it may set to be larger as the depth is larger.

Figure 17:
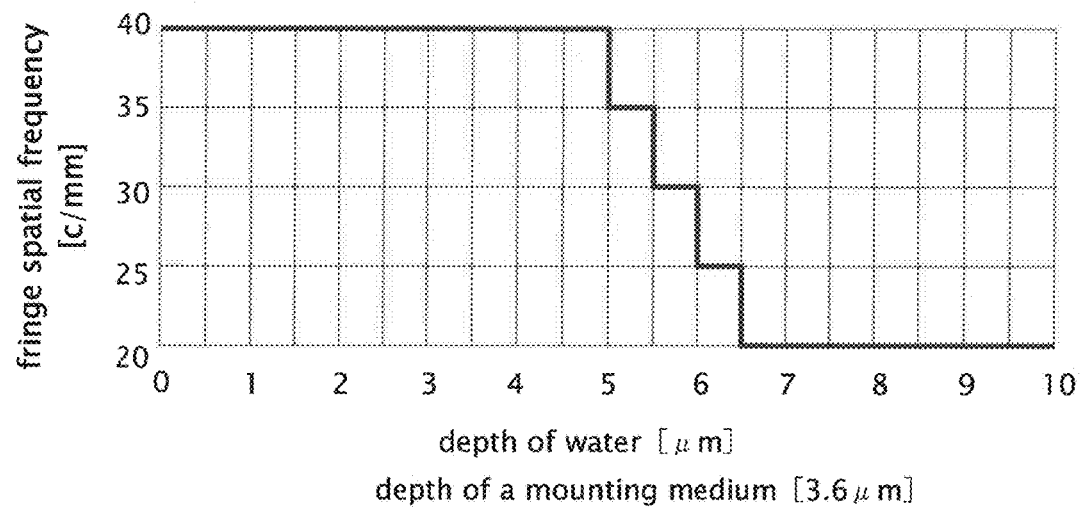
FIG. 17 is a diagram illustrating an example where the spatial frequency of the interference fringe is fixed when the depth of the observational object plane is smaller than a predetermined value.

For example, the spatial frequency of the interference fringe may be fixed when the depth of the observational object plane is a predetermined value or less, and the spatial frequency of the interference fringe may be changed only when the depth of the observational object plane exceeds the predetermined value (refer to FIG. 17).

In the first embodiment, the change pattern of the spatial frequency of the interference fringe with respect to the depth of the observational object plane is previously defined by the controlling device 39, but the change pattern may be previously specified by the user, or may be specified in real time by the user.

Figure 18:
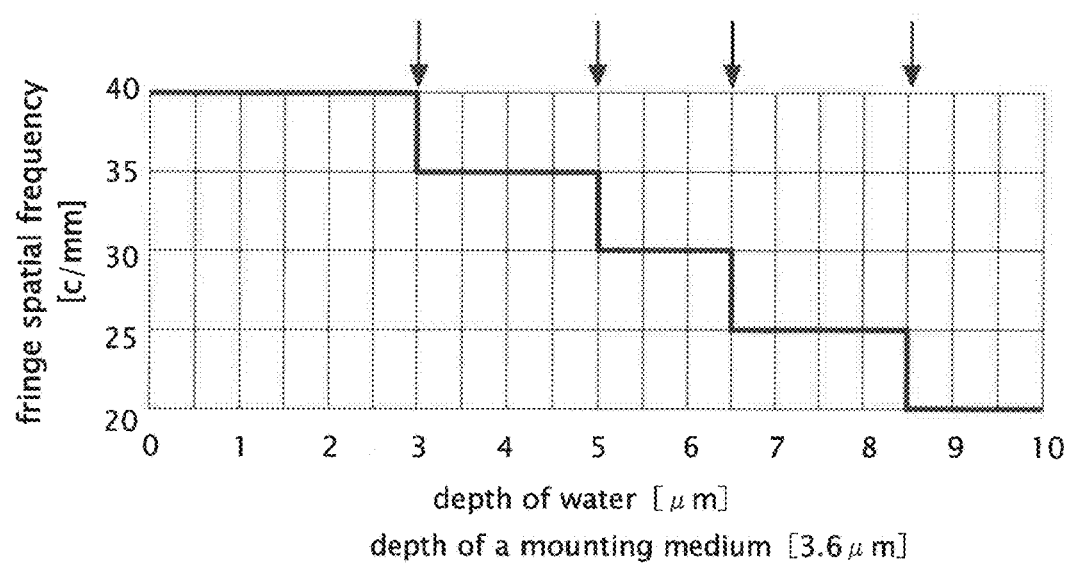
FIG. 18 is a diagram illustrating an example where a user specifies the change pattern of the spatial frequency of the interference fringe with respect to the depth of the observational object plane in real time.

Note that the controlling device 39 may repeat generation and display of the super-resolved image while making the depth of the observational object plane large, and the spatial frequency of the interference fringe may be switched to a lower value only at a timing when the user inputs a switching instruction so that the user specifies the change pattern in real time. FIG. 18 is a diagram illustrating a relationship between a timing when the user inputs the instruction and a change pattern. Each arrow in FIG. 18 indicates the timing when the user inputs the instruction. The user only observes the super-resolved image displayed in real time, and inputs the switching instruction of the spatial frequency of the interference fringe to the controlling device 39 at the timing when the image quality of the super-resolved image deteriorates, and thereby, the image quality of the super-resolved image can be kept.

In the first embodiment, the SLM 13 is disposed on the image conjugate plane in order to project the fringe on the observational object plane, and the grating pitch of the grating pattern displayed on the SLM 13 is switched in order to switch the spatial frequency of the fringe, but other methods may be used. Other methods are, for example, any of the following methods (1) to (4).

(1) A method in which a turret holding a plurality of diffraction gratings having different grating pitches are inserted into the image conjugate plane in order to project the fringe on the observational object plane, and the turret is rotated in order to switch the spatial frequency of the fringe. The turret is provided with a rotating mechanism to rotate the turret around a rotation shaft which is deviated from the optical axis AZ. The controlling device 39 drives this rotating mechanism. The diffraction grating which is simultaneously inserted into the optical path by the turret is only one of the plurality of diffraction gratings, and the plurality of diffraction gratings may be made of the same member, or made of mutually different members.

(2) A method in which a pair of exit ends of the optical fiber is disposed at symmetrical positions with respect to the optical axis AZ on the pupil conjugate plane in order to project the fringe on the observational object plane, and a height from the optical axis AZ to the pair of exit ends is switched in order to switch the spatial frequency of the fringe. Note that the height from the optical axis AZ to the pair of exit ends is adjusted by a mechanism such as a piezo element. The controlling device 39 drives this mechanism.

Figure 19A:
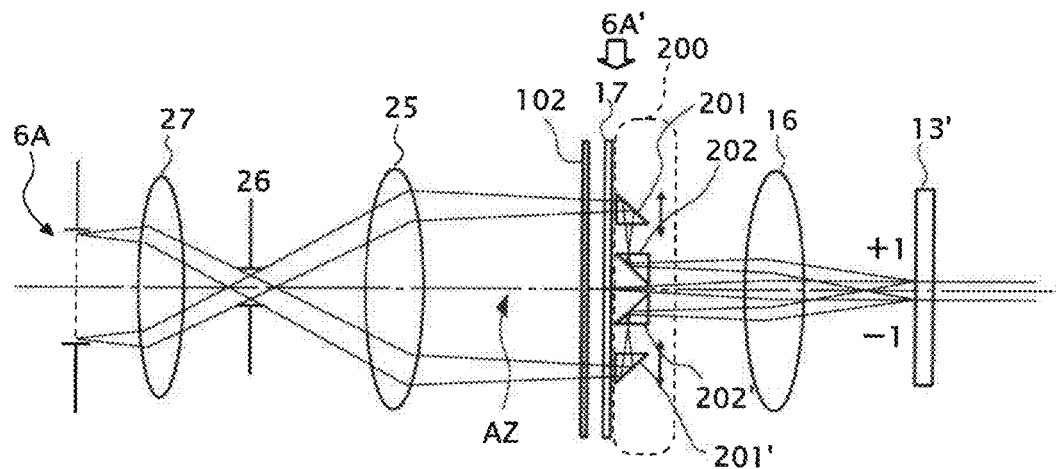
FIG. 19A is a diagram explaining a space adjusting part (an interval between prism mirrors is wide).
Figure 19B:
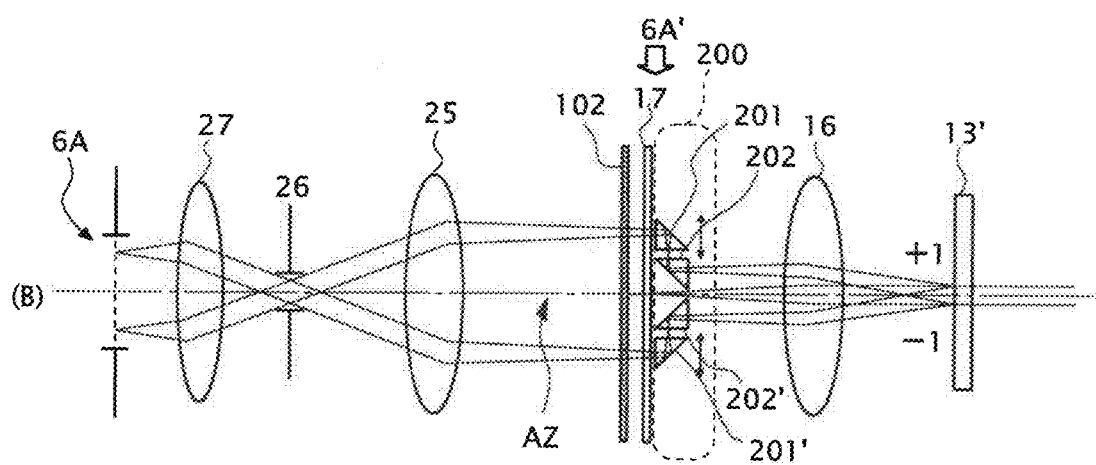
FIG. 19B is a diagrams explaining the space adjusting part (the interval between the prism mirrors is narrow)

(3) A method in which a diffraction grating whose grating pattern is constant is disposed on the image conjugate plane in order to project the fringe on the observational object plane, and the optical path space of the ±first-order diffractive light fluxes directed to the pupil plane 6A is adjusted by, for example, a space adjusting part 200 as illustrated in FIGS. 19A and 19B in order to switch the spatial frequency of the fringe. The controlling device 39 drives the mechanism of the space adjusting part.

Figure 20:
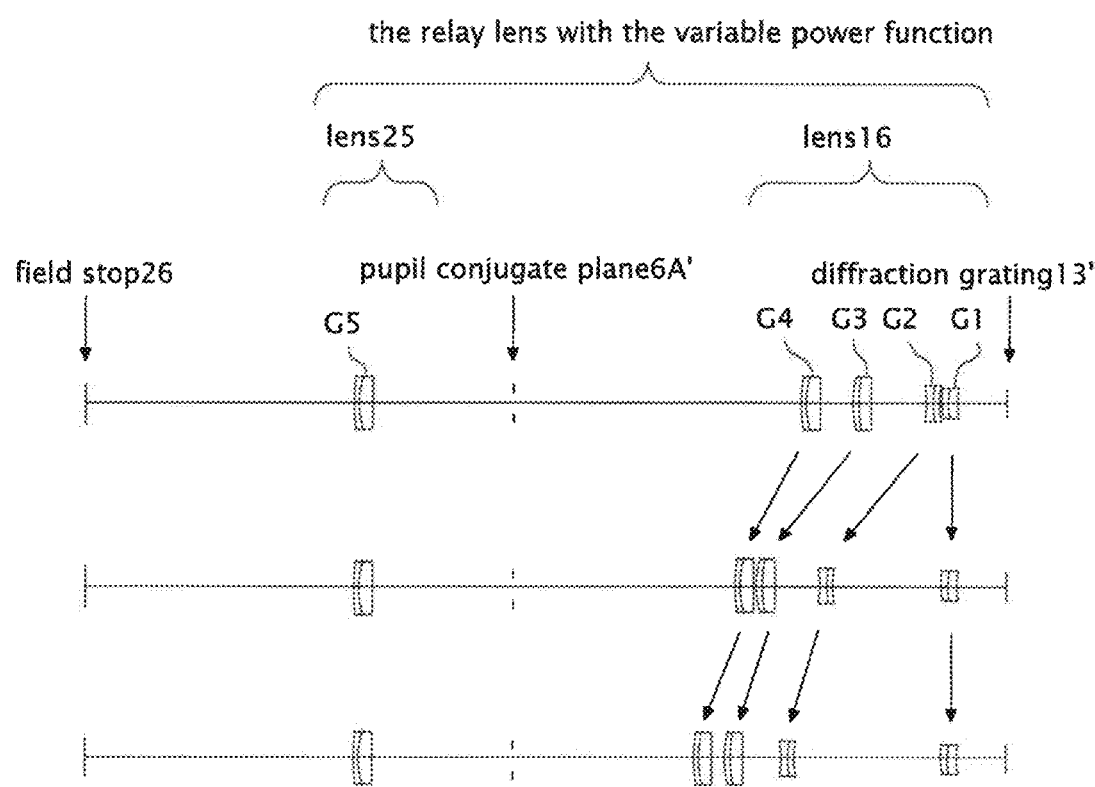
FIG. 20 is a diagram explaining a relay lens with a variable power function.

(4) A method in which a diffraction grating whose grating pattern is constant is disposed on the image conjugate plane in order to project the fringe on the observational object plane, and for example, a relay lens with a variable power function as illustrated in FIG. 20 is disposed between the diffraction grating and the specimen to perform a variable power operation in order to switch the spatial frequency of the fringe. The controlling device 39 drives a variable power adjusting mechanism (what is called a zoom adjusting mechanism) of the relay lens with the variable power function.

<Explanation of Space Adjusting Part>

Hereinafter, the space adjusting part 200 illustrated in FIGS. 19A and 19B is described.

First, a disposition target of the space adjusting part 200 is a place where the optical paths of the ±first-order diffractive light fluxes are separated from one another between the diffraction grating 13 whose grating pattern is constant and the observational object plane. Here, the disposition target of the space adjusting part 200 is set to in a vicinity of the pupil conjugate plane 6A' as illustrated in FIGS. 19A and 19B. A separation amount between the optical paths of the ±first-order diffractive light fluxes becomes a maximum in the vicinity of the pupil conjugate plane 6A'. Note that the ½-wavelength plate 101, the liquid crystal ½-wavelength plates 103, 104 are not illustrated out of the components of the beam selecting part 100 in the example in FIGS. 19A and 19B.

The space adjusting part 200 includes a prism mirror 202 which deflects the +first-order diffractive light flux incident from the collecting lens 16 side toward a direction separated from the optical axis AZ, and a prism mirror 201 which reflects the +first-order diffractive light flux deflected by the prism mirror 202 to return the direction of the optical path of the +first-order light flux to the original direction.

The space adjusting part 200 also includes a prism mirror 202' which deflects the −first-order diffractive light flux incident from the collecting lens 16 side toward a direction separated from the optical axis AZ, and a prism mirror 201' which reflects the −first-order diffractive light flux deflected by the prism mirror 202' to return the direction of the optical path of the −first-order light flux to the original direction.

Here, the optical paths of the ±first-order light fluxes which contribute to the interference fringe are necessary to be kept in a symmetrical relationship with respect to the optical axis AZ.

Accordingly, a disposition relationship of reflection planes of the prism mirrors 202, 202' at an upstream side of the space adjusting part 200 is kept in a symmetrical relationship with respect to the optical axis AZ, and a disposition relationship of reflection planes of the prism mirrors 201, 201' at a downstream side of the space adjusting part 200 is kept in a symmetrical relationship with respect to the optical axis AZ.

The prism mirrors 201, 201' at the downstream side of the space adjusting part 200 are able to change a space therebetween while keeping the mutual positional relationship in the symmetrical relationship with respect to the optical axis AZ as illustrated in FIG. 19A to FIG. 19B.

A space between collecting points of the ±first-order light fluxes on the pupil plane 6A can be adjusted by adjusting the space between the prism mirrors 201, 201' as above. The spatial frequency of the interference fringe is thereby adjusted. The "collecting point" described here means a barycenter position of an area having intensity of 80 percent or more of maximum intensity in an incident area of collected light.

The space adjusting part 200 includes a not-illustrated mechanism adjusting the space between the prism mirrors 201, 201', and the controlling device 39 drives the not-illustrated mechanism.

Since the space adjusting part 200 deflects the ±first-order diffractive light fluxes toward the direction separated from the optical axis AZ by the pair of prism mirrors 202, 202' disposed at the upstream side, a branch amount of the ±first-order diffractive light fluxes expands due to going through the space adjusting part 200. When a space adjusting amount is zero, the branch amount expands to the extent of a size of the prism. Accordingly, it is necessary to previously set the grating pitch of the diffraction grating 13' roughly in consideration of the expansion extent compared to a grating pitch which is necessary when the space adjusting part 200 does not exist.

In the above description, the space adjusting part 200 deflects the ±first-order diffractive light fluxes toward the direction separated from the optical axis AZ by the pair of prism mirrors 202, 202' disposed at the upstream side, but may deflect them toward a direction approaching the optical axis AZ. In this case, since the branch amount of the ±first-order diffractive light fluxes is reduced due to going through the space adjusting part 200, it is necessary to previously set the grating pitch of the diffraction grating 13' finely in consideration of the reduction extent.

<Explanation of Relay Lens with Variable Power Function>

Hereinafter, the relay lens with the variable power function illustrated in FIG. 20 is described. Here, it is assumed that the variable power function is supplied to the relay lens made of the collecting lenses 16, 25. The top, middle, and bottom in FIG. 20 each represent an example of a displacement pattern of a lens group due to a variable power operation. Note that a displacement direction of the lens group required for the variable power is a direction of the optical axis AZ.

As illustrated in FIG. 20, the collecting lens 16 is made of a first lens group G1 to a fourth lens group G4, and the collecting lens 25 is made of a fifth lens group G5. Among them, the first lens group G1 to the fourth lens group G4 are variable power optical systems each having the variable power function, and the fifth lens group G5 is an image-forming optical system having an image-forming function.

When disposition targets of the first lens group G1 to the fourth lens group G4 are changed as indicated by arrows, an image-forming magnification of the relay lens with the variable power function (collecting lenses 16, 25) is switched, and a pitch of the interference fringe is switched. The spatial frequency of the interference fringe is thereby regarded to be switched.

Note that the relay lens with the variable power function includes a not-illustrated variable power adjusting mechanism which interlocks the first lens group G1 to the fourth lens group G4, and the controlling device 39 drives the not-illustrated variable power adjusting mechanism.

Second Embodiment

Hereinafter, a modification example of the first embodiment is described as a second embodiment of the present invention. Here, only different points from the first embodiment are described.

Figure 21:
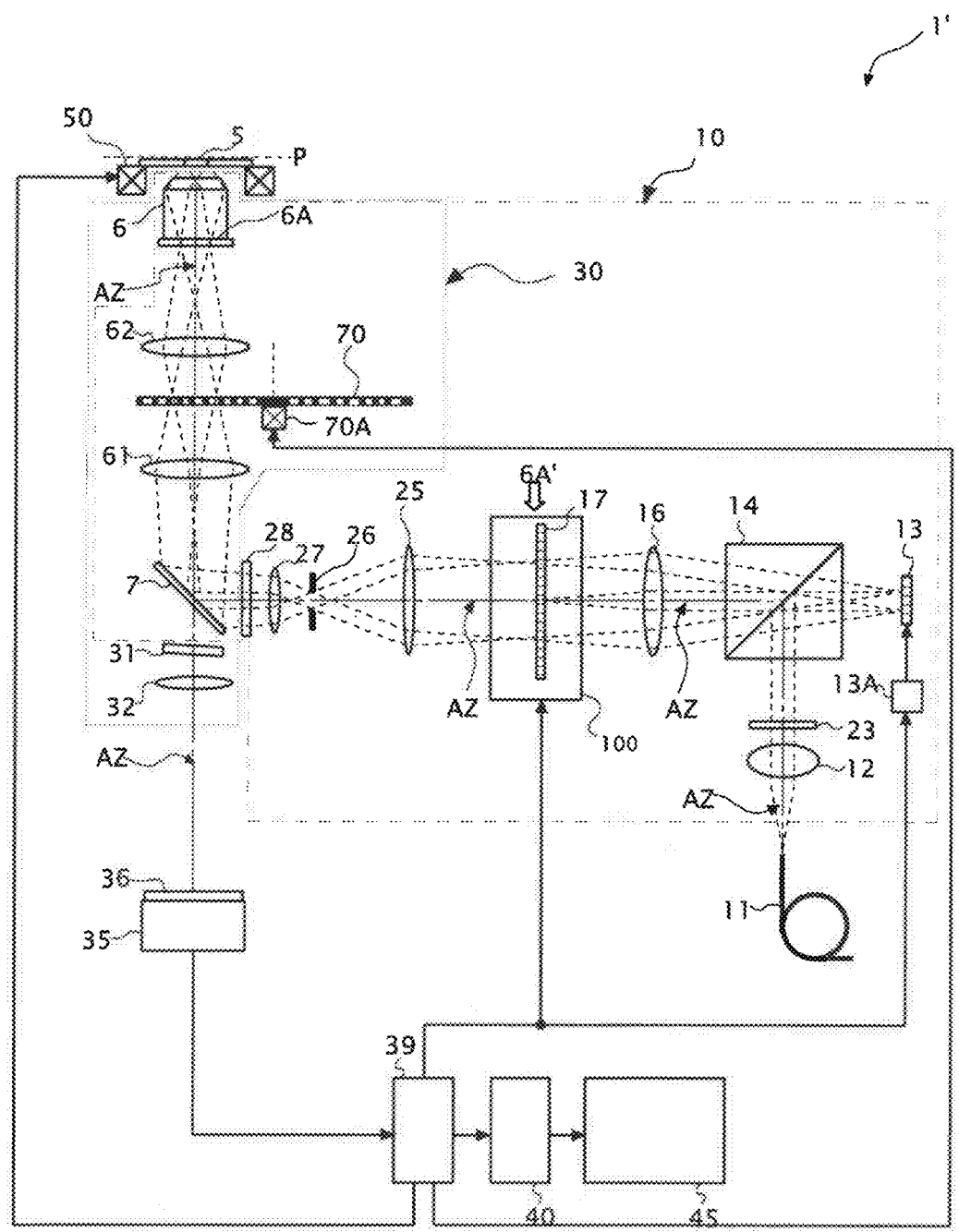
FIG. 21 is a configuration diagram of a 2D-SIM in a second embodiment.

FIG. 21 is a configuration diagram of a 2D-SIM1' (a structured illumination microscopy system 1) in this embodiment. In FIG. 21, the same reference numerals are supplied for the same component as ones illustrated in FIG. 1.

In the 2D-SIM1' of this embodiment, two collecting lenses 61, 62 forming a relay lens are disposed in sequence between the dichroic mirror 7 and the objective lens 6, and a rotating Nipkow disk 70 is inserted in an image conjugate plane between the two collecting lenses 61, 62. A rotating mechanism 70A is provided at the rotating Nipkow disk 70. The rotating mechanism 70A rotates the rotating Nipkow disk 70 around a rotation shaft which is in parallel with the optical axis AZ, and deviated from the optical axis AZ. The controlling device 39 drives this rotating mechanism 70A.

A lot of pinholes are formed at the rotating Nipkow disk 70 similar to a publicly-known Nipkow disk, and an arrangement pattern of the lot of pinholes is set such that proximity two points on the image conjugate plane are opened at mutually different timings, and a total opening amount of respective points on the image conjugate plane becomes uniform. An image can be acquired in shorter time as the number of pinholes is larger, but if an interval between the pinholes comes too close to approximate to a spatial resolution of an optical system, light quantity leaks out to an adjacent pinhole to lower sectioning performance.

The rotating Nipkow disk 70 performs an integer rotation within a period when the imaging sensor 35 captures a modulated image of one frame (exposure period). The rotating Nipkow disk 70 has a function of removing noise light generated at a non-observational object plane (=out-focused noise light).

There are advantages in the 2D-SIM1' of this embodiment that the above-stated second problem (the noise light generated at the non-observational object plane) is reduced and the SN ratio of the imaging sensor 35 can be improved.

In the first embodiment, the contrast of the interference fringe formed on the imaging plane 36 is set to a certain value or more (set to be 0.03 or more) in consideration of deterioration of the SN ratio of the imaging sensor 35.

However, in this embodiment, since the SN ratio of the imaging sensor 35 is improved, the interference fringe can be imaged even if the contrast of the interference fringe is further lowered compared to the contrast of the interference fringe in the first embodiment (0.03 or more).

Accordingly, in this embodiment, it is possible to set the spatial frequency of the interference fringe higher, a switching pitch of the spatial frequency rough, and to expand a maximum value of the depth of the observational object plane compared to the first embodiment.

Third Embodiment

Hereinafter, a modification example of the second embodiment is described as a third embodiment of the present invention. Here, only different points from the second embodiment are described.

Figure 22:
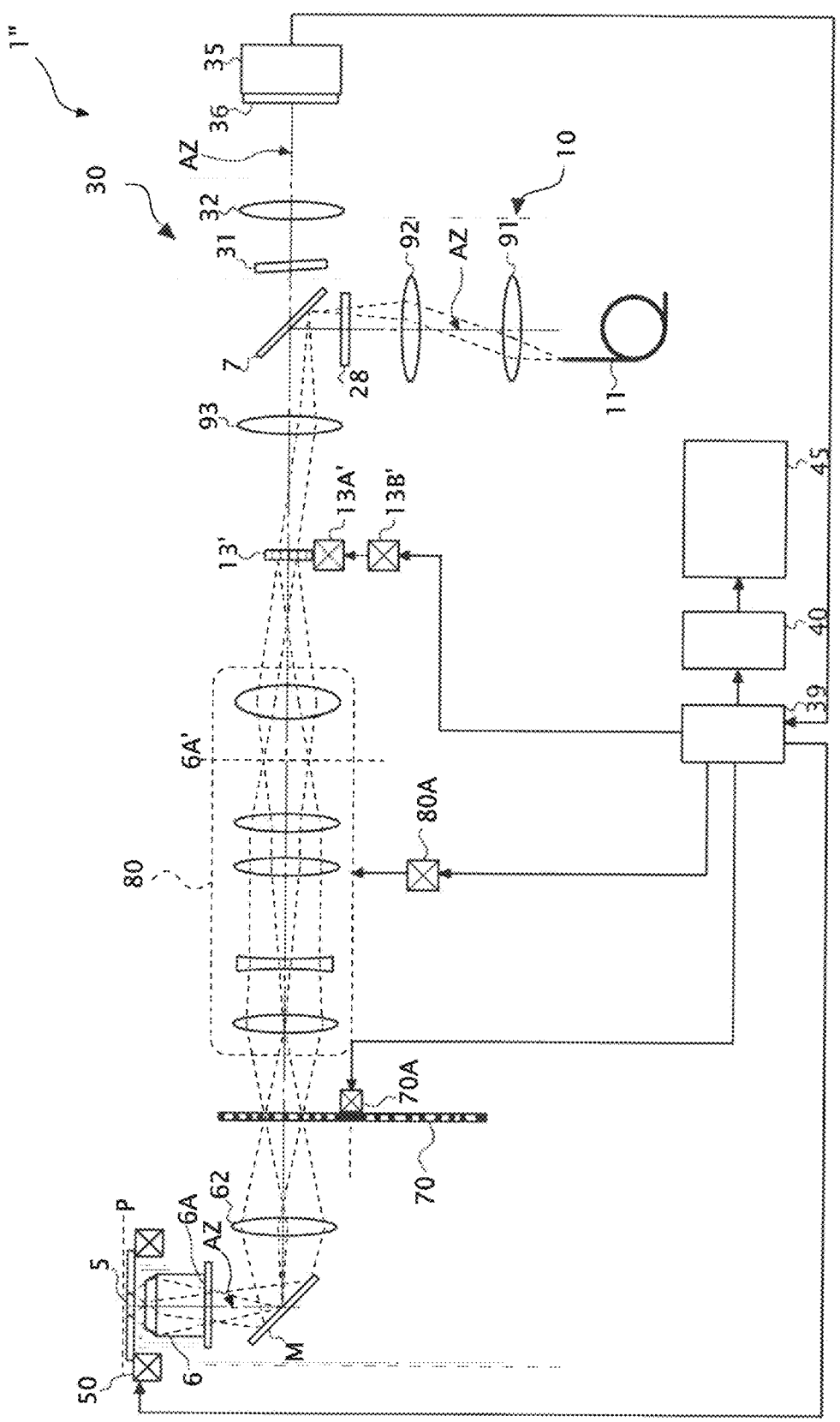
FIG. 22 is a configuration diagram of a 2D-SIM in a third embodiment.

FIG. 22 is a configuration diagram of a 2D-SIM1" (a structured illumination microscopy system 1") of this embodiment. In FIG. 22, the same reference numerals are supplied to the same components as ones illustrated in FIG. 21.

In this embodiment, a transmissive diffraction grating 13' whose grating pattern is constant is used instead of the SLM 13 being a reflective diffraction grating whose grating pattern is variable, and both the modulating function and the demodulating function of the fluorescence image are supplied to the diffraction grating 13'. That is, in this embodiment, the demodulation of the modulated image is not performed by the image storing-calculating device 40 by means of calculation but optically performed by the diffraction grating 13'.

First, both laser light from a light source and fluorescence from the specimen 5 are incident on the diffraction grating 13' in this embodiment. A disposition target of the dichroic mirror 7 which separates the laser light and the fluorescence is therefore set between the optical fiber 11 and the diffraction grating 13'. Each component from this dichroic mirror 7 to the objective lens 6 is used for both the illumination optical system 10 and the image-forming optical system 30.

In this embodiment, the beam selecting part 100 is not given, and instead thereof, an incident angle of the laser light with respect to the diffraction grating 13' is made large (made to be oblique incidence) to thereby deflect unnecessary diffractive light fluxes from an effective optical path.

Concretely, two light fluxes of the 0th-order diffractive light flux and the first-order diffractive light flux generated at the diffraction grating 13' are used as the diffractive light fluxes which contribute to the interference fringe (necessary diffractive light fluxes), and the −first-order diffractive light flux generated at the diffraction grating 13' is deflected from the optical path as the unnecessary diffractive light flux which does not contribute to the interference fringe.

In this embodiment, the variable power function is supplied to the relay lens 80 which projects the image of the diffraction grating 13' on the image conjugate plane in order to adjust the spatial frequency of the interference fringe instead of adjusting the grating pitch of the diffraction grating 13'. A reference numeral 80A is a variable power adjusting mechanism which performs a variable-power-operation of the relay lens 80 with the variable power function, and the controlling device 39 drives the variable power adjusting mechanism 80A.

In this embodiment, there are included a translatory shifting mechanism 13A' which translatory shifts the diffraction grating 13' in a grating pitch direction and a rotating mechanism 13B' which rotates the diffraction grating 13' and the translatory shifting mechanism 13A' around the optical axis AZ in order to switch the phase and the direction of the interference fringe. The controlling device 39 drives the translatory shifting mechanism 13A' and the rotating mechanism 13B'.

Hereinafter, behavior of light in this embodiment is described.

Laser light diverged from the exit end of the optical fiber 11 is incident on a collector lens 91 from a deflected position, then incident on a collecting lens 92 as a collimated light flux to be a converging light flux. The converging light flux is incident on the dichroic mirror 7 through the excitation filter 28, reflected by the dichroic mirror 7, and directed to a collecting lens 93. Since the dichroic mirror 7 is disposed in a vicinity of a rear side focal plane of the collecting lens 92, the converging light flux forms a collecting point in a vicinity of the dichroic mirror 7, exits from the collecting point as a divergent light flux to be incident on the collecting lens 93.

Since the dichroic mirror 7 is disposed in a vicinity of a front side focal plane of the collecting lens 93, the divergent light flux becomes the collimated light flux by being subjected to a collecting action of the collecting lens 93, and is incident on the diffraction grating 13' with a predetermined angle (oblique incidence).

At the diffraction grating 13', the 0th-order diffractive light flux and high-order diffractive light fluxes including the +first-order diffractive light flux are generated. Out of these diffractive light fluxes, the 0th-order diffractive light flux and the +first-order diffractive light flux are incident on the relay lens 80 with the variable power function, then form an image of the diffraction grating 13' on the rotating Nipkow disk 70 disposed at the image conjugate plane.

The relay lens 80 with the variable power function is designed such that a position of the pupil conjugate plane 6A' and a position of the image conjugate plane are kept independent of the variable power operation.

The 0th-order diffractive light flux and the +first-order diffractive light flux passing through the rotating Nipkow disk 70 become converging light fluxes by being subjected to the collecting action of the collecting lens 62 being a field lens, reflected by an all-reflective mirror M, and then collected toward mutually different positions of the pupil plane 6A of the objective lens 6. Incidentally, the collecting point of the 0th-order diffractive light flux and the collecting point of the +first-order diffractive light flux at the pupil plane 6A are symmetric with respect to the optical axis AZ.

The 0th-order diffractive light flux and the +first-order diffractive light flux exited from the pupil plane 6A exit from the tip of the objective lens 6 as the collimated light fluxes, are incident on the focal plane (=observational object plane P) of the objective lens 6 with a predetermined angle relationship, to form striped interference fringe.

The interference fringe is a secondary image of the diffraction grating 13' formed by the relay lens 80 with the variable power function, the field lens 62 and the objective lens 6. That is, all of the relay lens 80 with the variable power function, the field lens 62 and the objective lens 6 have a function of a "projecting optical system" projecting the image of the diffraction grating 13' on the observational object plane P.

Fluorescence generated at each position of the observational object plane P is incident on the tip of the objective lens 6, then exits from the pupil plane 6A of the objective lens 6 as a collimated light flux, and is incident on the relay lens 80 with the variable power function through the all-reflective mirror M, the field lens 62 and the rotating Nipkow disk 70. The fluorescence exited from the relay lens 80 with the variable power function forms a fluorescence image of the observational object plane P on the imaging plane 36 through the diffraction grating 13', the collecting lens 93, the dichroic mirror 7, the barrier filter 31 and the secondary objective lens 32. The controlling device 39 of this embodiment drives the translatory shifting mechanism 13A' within the exposure period of the imaging sensor 35, and shifts the diffraction grating 13' for an integral multiple of a period.

Since the fluorescence which contributes to the fluorescence image passes through the diffraction grating 13', the spatial frequency which is modulated by the interference fringe is resumed to an original spatial frequency in this fluorescence image. That is, this fluorescence image is a demodulated image.

The controlling device 39 of this embodiment is therefore able to acquire the image of the demodulated image (super-resolved image) by driving the imaging sensor 35 while the demodulated image is formed.

The super-resolved image in which a super-resolution effect is obtained in a single direction can be thereby acquired.

The controlling device 39 of this embodiment switches the direction of the diffraction grating 13' by driving the rotating mechanism 13B' and shifts the diffraction grating 13' for the integral multiple of the period by driving the translatory shifting mechanism 13A' within the exposure period of the imaging sensor 35 in each direction.

The super-resolved image in which the super-resolution effect is obtained in each direction can be thereby acquired. For example, it is possible to expand from the super-resolved image by each direction into a two-dimensional super-resolved image by using a method described in Specification of U.S. Pat. No. 8,081,378.

The controlling device 39 of this embodiment controls the spatial frequency of the interference fringe to a proper value by driving the mechanism 80A in accordance with the position of the observational object plane P in the depth direction. The control method of the spatial frequency of the interference fringe is as described above.

Accordingly, it is possible to obtain the similar effect as the second embodiment also in this embodiment.

Other Embodiments

In any of the above-stated embodiments, a part or all of the first problem (spherical aberration) may be corrected by an aberration correcting element such as an adaptive optics. The adaptive optics is an element disposed at the pupil conjugate plane or In the vicinity thereof to correct a wavefront shape of an incident light flux. In any of the above-stated embodiments, a correction amount distribution of the adaptive optics may be changed in accordance with the depth of the observational object plane.

In any of the above-stated embodiments, the present invention is applied to the 2D-SIM, but the present invention is applicable to a 3D-SIM. Though the light fluxes which contribute to the interference fringe are two-beam in the 2D-SIM, the light fluxes which contribute to the interference fringe are three-beam in the 3D-SIM.

When the 2D-SIM1 (FIG. 1) of the first embodiment or the 2D-SIM1' (FIG. 21) of the second embodiment is modified to the 3D-SIM, the cell of the SLM 17 in the vicinity of the optical axis AZ is set to an off-state by the beam selecting part 100 so as not to shield the 0th-order diffractive light flux by the fixed polarizing plate 102.

In the above-stated 2D-SIM, a combination of the two diffractive light fluxes to form the two-beam interference fringe is not limited to the above-stated combination.

Similarly, in the above-stated 3D-SIM, a combination of three diffractive light fluxes to form a three-beam interference fringe is not limited to the above-stated combination.

The illumination optical system 10 of the above-stated each embodiment is the epi-illumination optical system which illuminates the specimen 5 through the objective lens 6 of the image-forming optical system 30, but may be a transmissive or reflective illumination optical system which illuminates the specimen 5 (by a condenser lens) without being intervened by the objective lens 6.

In the above-stated each embodiment, the number of kinds of the fluorescent materials contained in the specimen 5 is assumed to be "one", but it may be "two or more". When a first fluorescent material and a second fluorescent material having different properties are contained in the specimen 5, the SIM of the above-stated each embodiment is modified as, for example, the following (1) to (4).

(1) A laser unit mounting a first laser light source and a second laser light source as a coherent light source is used. A wavelength of laser light exited from the first laser light source is the same as an excitation wavelength of the first fluorescent material, and a wavelength of laser light exited from the second laser light source is the same as an excitation wavelength of the second fluorescent material.

(2) A second dichroic mirror is disposed at a subsequent stage of the secondary objective lens 32. Properties of the second dichroic mirror are properties reflecting light with the same wavelength as a fluorescence wavelength of the first fluorescent material, and transmitting light with the same wavelength as a fluorescence wavelength of the second fluorescent material.

(3) A first imaging sensor and a second imaging sensor are used as the imaging sensor 35. A disposition target of the first imaging sensor is on an optical path of fluorescence reflected by the second dichroic mirror, and a disposition target of the second imaging sensor is on an optical path of fluorescence penetrating through the second dichroic mirror.

(4) A first barrier filter and a second barrier filter are used as the barrier filter 31. A disposition target of the first barrier filter is between the second dichroic mirror and the first imaging sensor, and a disposition target of the second barrier filter is between the second dichroic mirror and the second imaging sensor. Properties of the first barrier filter are set to properties transmitting light with the same wavelength as the fluorescence wavelength of the first fluorescent material, and shielding light with other wavelengths. Properties of the second barrier filter are set to properties transmitting light with the same wavelength as the fluorescence wavelength of the second fluorescent material, and shielding light with other wavelengths.

In the above-stated each embodiment, the present invention is applied to the SIM, but the present invention is applicable to other observation devices in which fringe is projected on a specimen.

For example, the present invention is applicable to an observation device proposed by Tony Wilson (Specification of U.S. Pat. No. 6,376,818). This observation device obtains an optical sectioning effect by projecting the fringe on the specimen. Since the first problem and the second problem may occur also in this observation device, the present invention is effective.

In the above-stated each embodiment, the spatial frequency is changed in accordance with the depth of the observational object plane, but the spatial frequency may be changed in accordance with a visual field (observation area) of the objective lens 6.

For example, there is a case when the visual field (observation area) of the objective lens 6 is switched on the observational object plane at a predetermined depth. In this case, there is a case when the index mismatch occurs in accordance with the observation area, and the image quality of the super-resolved image deteriorates. In such a case, the image quality of the super-resolved image can be improved as stated above by changing the spatial frequency in accordance with the observation area (the visual field of the objective lens 6). Note that the spatial frequency may be partially changed in the visual field (observation area) of the objective lens 6.

<Explanation of Demodulating Calculation>

Hereinafter, an example of the demodulating calculation is described. The demodulating calculation in the 2D-SIM is firstly described for the sake of simplicity.

When an intensity distribution of the structured illumination (fringe) in the 2D-SIM is assumed to be a sine wave made of only a single component of the spatial frequency K, a coordinate in a modulating direction (a fringe pitch direction) of the specimen is set as x, a fluorescence density distribution of the specimen is set as $O_r(x)$, and a point image intensity distribution of an optical system forming a specimen image is set as $P_r(x)$, the specimen image formed by the optical system is represented by the following expression (1).

$$I_r(x) = \sum_l m_l(O_r(x)\exp(ilKx + il\phi)) * P_r(x)) \quad (1)$$

Here, a symbol "." denotes a convolution integral, "φ" is a phase of the structured illumination, "l" is a modulation order (l=−1, 0, 1) by the structured illumination, and "$m_l$" is a modulation amplitude by the structured illumination.

A component corresponding to the modulation order l=0 in the expression (1) is a 0th-order modulated component which is not modulated by the structured illumination, and a component corresponding to the modulation order l=+1 is a +first-order modulated component (moire) which is modulated by the structured illumination, and a component corresponding to a modulation order l=−1 is the −first-order modulated component (moire) which is modulated by the structured illumination.

Hereinafter, a subscript "r" is added to an amount in a real space and a subscript "k" is added to an amount in a wave number space in order to distinguish between the amount in the real space and the amount in the wave number space.

Here, the expression (1) is Fourier transformed to be denoted by the wave number space, the following expression (2) is obtained. In this expression (2), $P_k(k)$ which is a Fourier conversion of the point image intensity distribution $P_r(x)$ is the MTF of the optical system.

$$I_k(k) = \sum_l m_l \exp(il\phi) O_k(k + lK) P_k(k) \quad (2)$$

In the expression (2), a −first-order modulated component $O_k(k-K)$ corresponding to the modulation order l=−1 and a +first-order modulated component $O_k(k+K)$ corresponding to the modulation order l=+1 correspond to ones where the actual spatial frequency of the specimen is shifted to an extent of the spatial frequency K of the structured illumination.

That is, according to the structured illumination having the spatial frequency K, a structure having a high spatial frequency exceeding the cutoff frequency of the optical system is transmitted to the image space. In addition, the super-resolution effect increases as the spatial frequency K of the structured illumination is higher. The spatial frequency K of the structured illumination may be therefore set to a value as large as possible being the cutoff frequency of the optical system or less in order to maximize the super-resolution effect.

According to the expression (2), since the 0th-order modulated component $O_k(k)$, the −first-order modulated component $\theta_k(k-K)$, and the +first-order modulated component $O_k(k+K)$ are mutually superimposed in the specimen image of the 2D-SIM, these components are necessary to be mutually separated in the demodulating calculation of the 2D-SIM.

The controlling device of the 2D-SIM therefore captures images for N times while fixing the spatial frequency K of the structured illumination, fixing the direction of the structured illumination, and shifting the phase φ of the structured illumination. N pieces of modulated images having a common spatial frequency component, a common modulation amplitude, and only the phases 4 of the structured illumination are different are thereby acquired.

A signal intensity $I_{kj}(k)$ of a j-th modulated image out of the N pieces of modulated images is represented by the following expression (3).

$$I_{kj}(k) = \sum_l m_l \exp(il\phi_j) O_k(k + lK) P_k(k) \quad (3)$$

Here, "$\phi_j$" in the expression (3) is a phase of the structured illumination in the J-th modulated image.

In the demodulating calculation of the 2D-SIM, the signal intensity of each of the N pieces of modulated images is applied to the expression (3) to thereby obtain N pieces of equations. In these N pieces of equations, three components of the −first-order modulated component $O_k(k-K)$, the 0th-order modulated component $O_k(k)$, and the +first-order modulated component $O_k(k+K)$ are unknown quantities.

The controlling device of the 2D-SIM therefore sets the number of pieces of the modulated images N to be N≥3. In the demodulating calculation of the 2D-SIM, the N pieces of modulated images are applied to the expression (3) to thereby obtain the N pieces (N≥3) of equations, and the −first-order modulated component $O_k(k-K)$, the 0th-order modulated component $O_k(k)$, and the +first-order modulated component $O_k(k+K)$ are made to be known quantities by simultaneously solving these N pieces of equations.

In the demodulating calculation of the 2D-SIM, each of the −first-order modulated component $O_k(k-K)$, the 0th-order modulated component $O_k(k)$, and the +first-order modulated component $O_k(k+K)$ may be made to be known quantities and then these components are divided by a value of $P_k(k)$ when the −first-order modulated component $O_k(k-K)$, the 0th-order modulated component $O_k(k)$, and the +first-order modulated component $O_k(k+K)$ are separated from one another. However, a publicly-known method which is less affected by noises such as a Wiener filter may be used instead of just performing the division.

When a non-structured illumination (uniform illumination) is used instead of the structured illumination, a range of the transmittable spatial frequency k by the MTF of the optical system ($-P_k(k)$) is $k=-2NA/\lambda$ to $2NA/\lambda$. Note that "$\lambda$" is the wavelength $\lambda$, and "NA" is the numerical aperture of the objective lens.

On the other hand, when the structured illumination of the 2D-SIM is used, the −first-order modulated component $O_k(k-K)$ contains structural information of a spatial frequency range of $(-2NA/\lambda-K)$ to $(2NA/\lambda-K)$, the 0th-order modulated component $O_k(k)$ contains structural information of a spatial frequency range of $(-2NA/\lambda)$ to $(2NA/\lambda)$, and the +first-order modulated component $O_k(k+K)$ contains structural information of a spatial frequency range of $(-2NA/\lambda+K)$ to $(2NA/\lambda+K)$.

Accordingly, all of the −first-order modulated component $O_k(k-K)$, the 0th-order modulated component $O_k(k)$, and the +first-order modulated component $O_k(k+K)$ contain the structural information of the spatial frequency range of $(-2NA/\lambda-K)$ to $(2NA/\lambda+K)$.

In the demodulating calculation of the 2D-SIM, the +first-order modulated component $O_k(k+K)$, the −first-order modulated component $O_k(k-K)$ are rearranged in the x direction to the extent of the spatial frequency K, and then the +first-order modulated component $O_k(k+K)$, the 0th-order modulated component $O_k(k)$, and the −first-order modulated component $O_k(k-K)$ are weight-synthesized on an identical frequency space, to thereby generate a demodulated image $O_k(x)$ whose spatial frequency range is expanded.

In the demodulating calculation of the 2D-SIM, the demodulated image $O_k(x)$ whose spatial frequency range is expanded is inverse-Fourier-transformed to thereby find a super-resolved image $O_r(x)$ of the specimen. This super-resolved image $O_r(x)$ has high resolution only in the modulating direction (x-direction).

The controlling device of the 2D-SIM therefore acquires the N pieces of modulated images in each of the plurality of structured illuminations having different directions in order to acquire high resolution in a plurality of directions. In the demodulating calculation of the 2D-SIM, the above-described processing is performed by each direction. In this case, respective components which are rearranged by directions are to be weight-synthesized on the identical frequency space.

Though the demodulating calculation of the 2D-SIM is described hereinabove, the demodulating calculation in the 3D-SIM is as described below.

Since the structured illumination of the 3D-SIM uses the three-beam interference fringes instead of the two-beam interference fringes, the demodulated components to be superimposed on the modulated image are five components of the 0th-order modulated component which is not modulated, ±second-order modulated components to be super-resolution components in a one-dimensional direction in a specimen plane and ±first-order modulated components to be the super-resolution components in the optical axis direction. Accordingly, the number of unknown quantities of the demodulating calculation in the 3D-SIM is five.

The controlling device of the 3D-SIM therefore sets N≥5, and the five components are made to be known quantities by simultaneously solving the N pieces (N≥5) of equations in the demodulating calculation of the 3D-SIM.

According to the 3D-SIM, the super-resolution effects can be obtained not only in the direction in the specimen plane but also in the optical axis direction.

The separation of the plurality of modulated components are performed by solving the simultaneous equations, but when N is large, the separation may be performed according to a method disclosed in Specification of U.S. Pat. No. 8,115,806 (a least-squares method).

Here, the processes of the rearrangement and the synthesis in the demodulating calculation are performed sequentially, but they may be performed by means of a collective arithmetic expression. The mathematical expression (1) in Online Methods described in the thesis of Gustafsson and so on (described below) or the like is applicable as the arithmetic expression.

Thesis of Gustafsson and so on: "Super-Resolution Video Microscopy of Live Cells by Structured Illumination", Peter Kner, Bryant B. Chhun, Eric R. Griffis, Lukman Winoto, and Mats G. L. Gustafsson, NATURE METHODS Vol. 6 NO. 5, pp. 339-342, (2009)

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A structured illumination microscopy system, comprising:
    an illumination optical system illuminating excitation light on a sample with an interference fringe, the excitation light being a light to excite a fluorescent material contained in the sample;
    a controlling part controlling a direction, a phase, and a spatial frequency of the interference fringe;
    an image-forming optical system forming an image of the sample which is modulated by illumination of the interference fringe;

an imaging sensor capturing the image formed by the image-forming optical system; and a demodulating part performing demodulation processing by using a plurality of images captured by the imaging sensor, wherein the controlling part controls the spatial frequency of the interference fringe in accordance with an illuminating position of the interference fringe in a depth direction of the sample.

2. The structured illumination microscopy system according to claim 1, wherein the depth direction is an optical axis direction of the illumination optical system.

3. The structured illumination microscopy system according to claim 1, wherein the illumination optical system includes an objective lens, and the controlling part controls the illuminating position of the interference fringe by controlling a focal position of the objective lens with respect to the sample.

4. The structured illumination microscopy system according to claim 3, wherein the controlling part changes the focal position of the objective lens along an optical axis direction, and the controlling part controls the spatial frequency of the interference fringe at each of at least two different focal positions to be mutually different.

5. The structured illumination microscopy system according to claim 3, wherein the controlling part controls the spatial frequency of the interference fringe at a first focal position to be smaller than the spatial frequency of the interference fringe at a second focal position positioned closer to the objective lens than the first focal position.

6. The structured illumination microscopy system according to claim 3, wherein the controlling part changes the focal position in the depth direction of the sample corresponding to an optical axis direction of the illumination optical system, and the controlling part controls the spatial frequency of the interference fringe at a first focal position to be larger than the spatial frequency of the interference fringe at a second focal position corresponding to a deeper position of the sample compared to the first focal position.

7. The structured illumination microscopy system according to claim 3, wherein the controlling part moves the focal position by every predetermined amount, in the depth direction of the sample corresponding to an optical axis direction of the illumination optical system, and the imaging sensor captures the image formed by the image-forming optical system at each focal position.

8. The structured illumination microscopy system according to claim 1, wherein the demodulating part categorizes images captured by the imaging sensor based on one of the spatial frequency of the interference fringe and the illuminating position of the interference fringe in the depth direction of the sample, and performs the demodulation processing by using a plurality of images belonging to a group being categorized.

9. A method comprising:

illuminating excitation light on a sample with an interference fringe, the excitation light being a light to excite a fluorescent material contained in the sample;

controlling a direction, a phase, and a spatial frequency of the interference fringe;

capturing images of the sample modulated by illumination of the interference fringe;

performing demodulation processing by using a plurality of images being captured; and controlling the spatial frequency of the interference fringe in accordance with an illuminating position of the interference fringe in a depth direction of the sample.

10. A non-transitory storage medium storing a program causing a computer to execute processing comprising controlling a spatial frequency of an interference fringe in accordance with an illuminating position of the interference fringe in a depth direction of the sample, in a structured illumination microscopy system which captures an image of the sample modulated by illumination of the interference fringe and performs demodulation processing.

11. The structured illumination microscopy system according to claim 1, wherein the image-forming optical system comprises an objective lens, and the controlling part sets the spatial frequency to a proper value based on a medium, which exists from the objective lens to the illuminating position, and the illuminating position of the interference fringe in the optical axis direction of the illumination optical system.

12. The structured illumination microscopy system according to claim 11, wherein the medium includes at least one of an immersion liquid and a culture fluid of the sample.

13. The structured illumination microscopy system according to claim 11, wherein the medium is a combination of an immersion liquid and a culture fluid of the sample.

14. The structured illumination microscopy system according to claim 11, wherein the controlling part sets the spatial frequency of the interference fringe to the proper value based on a relationship between the medium and the illuminating position, and the spatial frequency of the interference fringe is set so as to be in a range at which a contrast of the interference fringe is a certain value or more.

* * * * *